United States Patent
Wender et al.

(10) Patent No.: US 7,585,834 B2
(45) Date of Patent: *Sep. 8, 2009

(54) TRANSPORTERS COMPRISING SPACED ARGININE MOIETIES

(75) Inventors: Paul A. Wender, Menlo Park, CA (US); Jonathan B. Rothbard, Cupertino, CA (US); Lee Wright, Redwood City, CA (US); Erik L. Kreider, Sunnyvale, CA (US); Christopher L. VanDeusen, Columbus, CA (US)

(73) Assignees: The Board of Trustees of the Leland Stanford Junior University, Stanford, CA (US); Cellgate, Inc., Sunnyvale, CA (US)

( * ) Notice: Subject to any disclaimer, the term of this patent is extended or adjusted under 35 U.S.C. 154(b) by 502 days.

This patent is subject to a terminal disclaimer.

(21) Appl. No.: 10/078,247

(22) Filed: Feb. 14, 2002

(65) Prior Publication Data

US 2003/0032593 A1 Feb. 13, 2003

Related U.S. Application Data

(60) Provisional application No. 60/269,627, filed on Feb. 16, 2001.

(51) Int. Cl.
*A61K 38/00* (2006.01)
*C12P 13/10* (2006.01)
(52) U.S. Cl. .............................. 514/2; 530/300; 435/114
(58) Field of Classification Search .................. None
See application file for complete search history.

(56) References Cited

U.S. PATENT DOCUMENTS

| | | | | |
|---|---|---|---|---|
| 4,409,141 | A * | 10/1983 | Noda et al. | 530/324 |
| 5,866,123 | A | 2/1999 | MacLeod | |
| 6,548,651 | B1 | 4/2003 | Nielsen et al. | |
| 6,593,292 | B1 * | 7/2003 | Rothbard et al. | 514/2 |
| 6,669,951 | B2 * | 12/2003 | Rothbard et al. | 424/436 |
| 6,730,293 | B1 * | 5/2004 | Rothbard et al. | 424/78.05 |
| 7,070,807 | B2 * | 7/2006 | Mixson | 424/484 |
| 7,229,961 | B2 * | 6/2007 | Rothbard et al. | 514/2 |

FOREIGN PATENT DOCUMENTS

| WO | WO 79/00515 | 8/1979 |
|---|---|---|
| WO | WO 91/09958 | 7/1991 |
| WO | WO 94/04686 | 3/1994 |
| WO | WO 98/52614 | 11/1998 |
| WO | WO 00/74701 | 12/2000 |
| WO | WO 01/13957 | 3/2001 |
| WO | WO 01/62297 | 8/2001 |
| WO | WO 02/069930 | 9/2002 |

OTHER PUBLICATIONS

Lorenzen, et al., The Journal of Cell Biology, 1995, 131, 631-643.*
Olsson, et al., Biochimica et Biophysica Acta, 1991, 1097, 37-44.*
Reimekasten, 1998, J. Clin. Invest., 102, 754-763.*
Brigidou et al. (1995), "The Retro-Inverso Form of a Homeobox-Derived Short Peptide is Rapidly Internalised by Cultured Neurones: A New Basis for an Efficient Intracellular Delivery System," *Biochemical and Biophysical Research Communications* 214(2):685-693.
Burnette (1989), "Iontophoresis," *Developmental Issues and Research Initiatives*, Chapter 11, pp. 247-291, Hadgraft (Ed.), Marcel Dekker.
Mi et al. (2000), "Characterization of a Class of Cationic Peptides Able to Facilitate Efficient Protein Transduction in Vivo and in Vitro," *Molecular Therapy* 2(4):339-347.
Morris et al. (2001), "A Peptide Carrier for the Delivery of Biologically Active Proteins Into Mammalian Cells," *Nature Biotechnology* 19:1173-1176.

* cited by examiner

*Primary Examiner*—Andrew D Kosar
*Assistant Examiner*—Satyanarayana R Gudibande
(74) *Attorney, Agent, or Firm*—Mintz, Levin, Cohn, Ferris, Glovsky and Popeo, PC

(57) ABSTRACT

The present invention provides compositions and methods for enhancing transport of biologically active compounds across biological membranes and across and into animal epithelial or endothelial tissues. The composition includes a biologically active agent and a transport moiety. The transport moiety includes a structure selected from the group consisting of $(ZYZ)_nZ$, $(ZY)_nZ$, $(ZYY)_nZ$ and $(ZYYY)_nZ$. Subunit "Z" is L-arginine or D-arginine, and subunit "Y" is an amino acid that does not comprise an amidino or guanidino moiety. Subscript "n" is an integer ranging from 2 to 10. The method for enhancing transport involves the administration of the aforementioned composition.

33 Claims, 15 Drawing Sheets

| | | | | | | | | | | | |
|---|---|---|---|---|---|---|---|---|---|---|---|
| Arg | Arg | Arg | Arg | Arg | Arg | Arg | | | | | |
| Arg | Aca | Arg | Arg | Arg | Arg | Arg | Arg | | | | |
| Arg | Arg | Aca | Arg | Arg | Arg | Arg | Arg | | | | |
| Arg | Arg | Arg | Aca | Arg | Arg | Arg | Arg | | | | 1:6 Octa |
| Arg | Arg | Arg | Arg | Aca | Arg | Arg | Arg | | | | |
| Arg | Arg | Arg | Arg | Arg | Aca | Arg | Arg | | | | |
| Arg | Arg | Arg | Arg | Arg | Arg | Aca | Arg | | | | |
| Arg | Aca | Arg | Aca | Arg | Arg | Arg | Arg | Arg | | | |
| Arg | Aca | Arg | Arg | Aca | Arg | Arg | Arg | Arg | | | |
| Arg | Aca | Arg | Arg | Arg | Aca | Arg | Arg | Arg | | | |
| Arg | Aca | Arg | Arg | Arg | Arg | Aca | Arg | Arg | | | |
| Arg | Aca | Arg | Arg | Arg | Arg | Arg | Aca | Arg | | | |
| Arg | Arg | Aca | Arg | Aca | Arg | Arg | Arg | Arg | | | |
| Arg | Arg | Aca | Arg | Arg | Aca | Arg | Arg | Arg | | | |
| Arg | Arg | Aca | Arg | Arg | Arg | Aca | Arg | Arg | | | 2:15 Nona |
| Arg | Arg | Aca | Arg | Arg | Arg | Arg | Aca | Arg | | | |
| Arg | Arg | Arg | Aca | Arg | Aca | Arg | Arg | Arg | | | |
| Arg | Arg | Arg | Aca | Arg | Arg | Aca | Arg | Arg | | | |
| Arg | Arg | Arg | Aca | Arg | Arg | Arg | Aca | Arg | | | |
| Arg | Arg | Arg | Arg | Aca | Arg | Aca | Arg | Arg | | | |
| Arg | Arg | Arg | Arg | Aca | Arg | Arg | Aca | Arg | | | |
| Arg | Arg | Arg | Arg | Arg | Aca | Arg | Aca | Arg | | | |
| Arg | Aca | Arg | Aca | Arg | Aca | Arg | Arg | Arg | | | |
| Arg | Aca | Arg | Arg | Aca | Arg | Aca | Arg | Arg | | | |
| Arg | Aca | Arg | Arg | Aca | Arg | Arg | Aca | Arg | | | |
| Arg | Aca | Arg | Arg | Aca | Arg | Arg | Arg | Aca | | | |
| Arg | Aca | Arg | Arg | Arg | Aca | Arg | Aca | Arg | | | |
| Arg | Aca | Arg | Arg | Arg | Aca | Arg | Arg | Aca | | | |
| Arg | Arg | Aca | Arg | Aca | Arg | Aca | Arg | Arg | | | |
| Arg | Arg | Aca | Arg | Aca | Arg | Arg | Aca | Arg | | | 3:16 Deca |
| Arg | Arg | Aca | Arg | Aca | Arg | Arg | Arg | Aca | | | |
| Arg | Arg | Aca | Arg | Arg | Aca | Arg | Aca | Arg | | | |
| Arg | Arg | Aca | Arg | Arg | Aca | Arg | Arg | Aca | | | |
| Arg | Arg | Aca | Arg | Arg | Arg | Aca | Aca | Arg | | | |
| Arg | Arg | Arg | Aca | Arg | Aca | Arg | Aca | Arg | | | |
| Arg | Arg | Arg | Aca | Arg | Aca | Arg | Arg | Aca | | | |
| Arg | Arg | Arg | Aca | Arg | Arg | Aca | Aca | Arg | | | |
| Arg | Arg | Arg | Arg | Aca | Arg | Aca | Aca | Arg | | | |
| Arg | Aca | Arg | Aca | Arg | Aca | Arg | Aca | Arg | Arg | | |
| Arg | Aca | Arg | Aca | Arg | Aca | Arg | Arg | Aca | Arg | | |
| Arg | Aca | Arg | Aca | Arg | Aca | Arg | Arg | Arg | Aca | | |
| Arg | Aca | Arg | Aca | Arg | Arg | Aca | Arg | Aca | Arg | | |
| Arg | Aca | Arg | Aca | Arg | Arg | Aca | Arg | Arg | Aca | | |
| Arg | Aca | Arg | Aca | Arg | Arg | Arg | Aca | Aca | Arg | | |
| Arg | Aca | Arg | Arg | Aca | Arg | Aca | Arg | Aca | Arg | | |
| Arg | Aca | Arg | Arg | Aca | Arg | Aca | Arg | Arg | Aca | | |
| Arg | Aca | Arg | Arg | Aca | Arg | Arg | Aca | Aca | Arg | | 4:15 Undeca |
| Arg | Aca | Arg | Arg | Arg | Aca | Arg | Aca | Aca | Arg | | |
| Arg | Arg | Aca | Arg | Aca | Arg | Aca | Arg | Aca | Arg | | |
| Arg | Arg | Aca | Arg | Aca | Arg | Aca | Arg | Arg | Aca | | |
| Arg | Arg | Aca | Arg | Aca | Arg | Arg | Aca | Aca | Arg | | |
| Arg | Arg | Aca | Arg | Arg | Aca | Arg | Aca | Aca | Arg | | |
| Arg | Arg | Arg | Aca | Arg | Aca | Arg | Aca | Aca | Arg | | |
| Arg | Aca | Arg | Aca | Arg | Aca | Arg | Aca | Arg | Arg | | |
| Arg | Aca | Arg | Aca | Arg | Aca | Arg | Arg | Aca | Arg | | |
| Arg | Aca | Arg | Aca | Arg | Aca | Arg | Arg | Aca | Arg | | |
| Arg | Aca | Arg | Aca | Arg | Arg | Aca | Arg | Aca | Arg | | 5:6 Dodeca |
| Arg | Aca | Arg | Arg | Aca | Arg | Aca | Arg | Aca | Arg | | |
| Arg | Arg | Aca | Arg | Aca | Arg | Aca | Arg | Aca | Arg | | |
| Arg | Aca | Arg | Aca | Arg | Aca | Arg | Aca | Arg | Aca | Arg | 6:1 Trideca |

FIG. 7

SEQUENCE LISTING

```
<160> NUMBER OF SEQ ID NOS: 30

<210> SEQ ID NO 1
<211> LENGTH: 9
<212> TYPE: PRT
<213> ORGANISM: Artificial
<220> FEATURE:
<223> OTHER INFORMATION: Chemically synthesized peptide

<400> SEQUENCE: 1

Arg Lys Lys Arg Arg Gln Arg Arg Arg
1               5

<210> SEQ ID NO 2
<211> LENGTH: 8
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
```

```
<223> OTHER INFORMATION: fluorescein isothiocyanate modified N-terminus
<220> FEATURE:
<221> NAME/KEY: AMIDATION
<222> LOCATION: (8)..(8)

<400> SEQUENCE: 2

Xaa Arg Arg Arg Arg Arg Arg Arg
1               5

<210> SEQ ID NO 3
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 3

Xaa Arg Arg Arg Arg Arg Arg Arg Arg Arg Arg
1               5                   10

<210> SEQ ID NO 4
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 4

Xaa Arg Gly Arg Arg Gly Arg Arg Gly Arg Arg
1               5                   10

<210> SEQ ID NO 5
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: MOD_RES
<222> LOCATION: (3)..(3)
<223> OTHER INFORMATION: Xaa is aminobutyric acid
<220> FEATURE:
<221> NAME/KEY: MOD_RES
```

<222> LOCATION: (6)..(6)
<223> OTHER INFORMATION: Xaa is aminobutyric acid
<220> FEATURE:
<221> NAME/KEY: MOD_RES
<222> LOCATION: (9)..(9)
<223> OTHER INFORMATION: Xaa is aminobutyric acid
<220> FEATURE:
<221> NAME/KEY: AMIDATION
<222> LOCATION: (11)..(11)

<400> SEQUENCE: 5

Xaa Arg Xaa Arg Arg Xaa Arg Arg Xaa Arg Arg
1               5                   10

<210> SEQ ID NO 6
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: MOD_RES
<222> LOCATION: (3)..(3)
<223> OTHER INFORMATION: Xaa is aminocaproic acid
<220> FEATURE:
<221> NAME/KEY: MOD_RES
<222> LOCATION: (6)..(6)
<223> OTHER INFORMATION: Xaa is aminocaproic acid
<220> FEATURE:
<221> NAME/KEY: MOD_RES
<222> LOCATION: (9)..(9)
<223> OTHER INFORMATION: Xaa is aminocaproic acid
<220> FEATURE:
<221> NAME/KEY: AMIDATION
<222> LOCATION: (11)..(11)

<400> SEQUENCE: 6

Xaa Arg Xaa Arg Arg Xaa Arg Arg Xaa Arg Arg
1               5                   10

<210> SEQ ID NO 7
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 7

Xaa Arg Ala Arg Arg Ala Arg Arg Ala Arg Arg
1               5                   10

<210> SEQ ID NO 8
<211> LENGTH: 11
<212> TYPE: PRT

```
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 8

Xaa Arg Asp Arg Arg Asp Arg Arg Asp Arg Arg
1               5                   10

<210> SEQ ID NO 9
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 9

Xaa Arg Glu Arg Arg Glu Arg Arg Glu Arg Arg
1               5                   10

<210> SEQ ID NO 10
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 10

Xaa Arg Phe Arg Arg Phe Arg Arg Phe Arg Arg
1               5                   10

<210> SEQ ID NO 11
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
```

```
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 11

Xaa Arg His Arg Arg His Arg Arg His Arg Arg
1               5                   10

<210> SEQ ID NO 12
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 12

Xaa Arg Ile Arg Arg Ile Arg Arg Ile Arg Arg
1               5                   10

<210> SEQ ID NO 13
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 13

Xaa Arg Lys Arg Arg Lys Arg Arg Lys Arg Arg
1               5                   10

<210> SEQ ID NO 14
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)
```

-continued

```
<400> SEQUENCE: 14

Xaa Arg Leu Arg Arg Leu Arg Arg Leu Arg Arg
1               5                   10

<210> SEQ ID NO 15
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 15

Xaa Arg Met Arg Arg Met Arg Arg Met Arg Arg
1               5                   10

<210> SEQ ID NO 16
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 16

Xaa Arg Asn Arg Arg Asn Arg Arg Asn Arg Arg
1               5                   10

<210> SEQ ID NO 17
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 17

Xaa Arg Pro Arg Arg Pro Arg Arg Pro Arg Arg
1               5                   10
```

<210> SEQ ID NO 18
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 18

Xaa Arg Gln Arg Arg Gln Arg Arg Gln Arg Arg
1               5                   10

<210> SEQ ID NO 19
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 19

Xaa Arg Ser Arg Arg Ser Arg Arg Ser Arg Arg
1               5                   10

<210> SEQ ID NO 20
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 20

Xaa Arg Thr Arg Arg Thr Arg Arg Thr Arg Arg
1               5                   10

<210> SEQ ID NO 21
<211> LENGTH: 11
<212> TYPE: PRT
<213> ORGANISM: Artificial
<220> FEATURE:
<223> OTHER INFORMATION: Chemically synthesized peptide
<220> FEATURE:

```
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 21

Xaa Arg Val Arg Arg Val Arg Arg Val Arg Arg
1               5                   10

<210> SEQ ID NO 22
<211> LENGTH: 11
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (11)..(11)

<400> SEQUENCE: 22

Xaa Arg Tyr Arg Arg Tyr Arg Arg Tyr Arg Arg
1               5                   10

<210> SEQ ID NO 23
<211> LENGTH: 10
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: MOD_RES
<222> LOCATION: (3)..(3)
<223> OTHER INFORMATION: Xaa is aminocaproic acid
<220> FEATURE:
<221> NAME/KEY: MOD_RES
<222> LOCATION: (5)..(5)
<223> OTHER INFORMATION: Xaa is aminocaproic acid
<220> FEATURE:
<221> NAME/KEY: MOD_RES
<222> LOCATION: (7)..(7)
<223> OTHER INFORMATION: Xaa is aminocaproic acid
<220> FEATURE:
<221> NAME/KEY: MOD_RES
<222> LOCATION: (9)..(9)
<223> OTHER INFORMATION: Xaa is aminocaproic acid
<220> FEATURE:
<221> NAME/KEY: AMIDATION
<222> LOCATION: (10)..(10)

<400> SEQUENCE: 23

Xaa Arg Xaa Arg Xaa Arg Xaa Arg Xaa Arg
1               5                   10
```

<210> SEQ ID NO 24
<211> LENGTH: 12
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: MOD_RES
<222> LOCATION: (3)..(3)
<223> OTHER INFORMATION: Xaa is aminocaproic acid
<220> FEATURE:
<221> NAME/KEY: MOD_RES
<222> LOCATION: (5)..(5)
<223> OTHER INFORMATION: Xaa is aminocaproic acid
<220> FEATURE:
<221> NAME/KEY: MOD_RES
<222> LOCATION: (7)..(7)
<223> OTHER INFORMATION: Xaa is aminocaproic acid
<220> FEATURE:
<221> NAME/KEY: MOD_RES
<222> LOCATION: (9)..(9)
<223> OTHER INFORMATION: Xaa is aminocaproic acid
<220> FEATURE:
<221> NAME/KEY: MOD_RES
<222> LOCATION: (11)..(11)
<223> OTHER INFORMATION: Xaa is aminocaproic acid
<220> FEATURE:
<221> NAME/KEY: AMIDATION
<222> LOCATION: (12)..(12)

<400> SEQUENCE: 24

Xaa Arg Xaa Arg Xaa Arg Xaa Arg Xaa Arg Xaa Arg
1               5                   10

<210> SEQ ID NO 25
<211> LENGTH: 14
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: MOD_RES
<222> LOCATION: (3)..(3)
<223> OTHER INFORMATION: Xaa is aminocaproic acid
<220> FEATURE:
<221> NAME/KEY: MOD_RES
<222> LOCATION: (5)..(5)
<223> OTHER INFORMATION: Xaa is aminocaproic acid
<220> FEATURE:
<221> NAME/KEY: MOD_RES
<222> LOCATION: (7)..(7)
<223> OTHER INFORMATION: Xaa is aminocaproic acid
<220> FEATURE:
<221> NAME/KEY: MOD_RES
<222> LOCATION: (9)..(9)
<223> OTHER INFORMATION: Xaa is aminocaproic acid
<220> FEATURE:
<221> NAME/KEY: MOD_RES
<222> LOCATION: (11)..(11)

```
<223> OTHER INFORMATION: Xaa is aminocaproic acid
<220> FEATURE:
<221> NAME/KEY: MOD_RES
<222> LOCATION: (13)..(13)
<223> OTHER INFORMATION: Xaa is aminocaproic acid
<220> FEATURE:
<221> NAME/KEY: AMIDATION
<222> LOCATION: (14)..(14)

<400> SEQUENCE: 25

Xaa Arg Xaa Arg Xaa Arg Xaa Arg Xaa Arg Xaa Arg Xaa Arg
1               5                   10

<210> SEQ ID NO 26
<211> LENGTH: 20
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (20)..(20)

<400> SEQUENCE: 26

Xaa Arg Gly Gly Arg Gly Gly Arg Gly Gly Arg Gly Gly Arg Gly Gly
1               5                   10                  15

Arg Gly Gly Arg
            20

<210> SEQ ID NO 27
<211> LENGTH: 14
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (14)..(14)

<400> SEQUENCE: 27

Xaa Arg Gly Arg Gly Arg Gly Arg Gly Arg Gly Arg Gly Arg
1               5                   10

<210> SEQ ID NO 28
<211> LENGTH: 13
<212> TYPE: PRT
<213> ORGANISM: Artificial
<220> FEATURE:
<223> OTHER INFORMATION: Chemically synthesized peptide

<400> SEQUENCE: 28

Arg Arg Arg Arg Arg Arg Arg Arg Arg Arg Arg Arg Arg
1               5                   10
```

```
<210> SEQ ID NO 29
<211> LENGTH: 19
<212> TYPE: PRT
<213> ORGANISM: Artificial
<220> FEATURE:
<223> OTHER INFORMATION: Chemically synthesized peptide

<400> SEQUENCE: 29

Arg Arg Arg Arg Arg Arg Arg Arg Arg Arg Arg Arg Arg Arg Arg Arg
1               5                   10                  15

Arg Arg Arg

<210> SEQ ID NO 30
<211> LENGTH: 26
<212> TYPE: PRT
<213> ORGANISM: Artificial
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: Xaa is aminocaproic acid
<220> FEATURE:
<221> NAME/KEY: MOD_RES
<222> LOCATION: (1)..(1)
<223> OTHER INFORMATION: fluorescein isothiocyanate modified N-terminus
<220> FEATURE:
<221> NAME/KEY: AMIDATION
<222> LOCATION: (26)..(26)

<400> SEQUENCE: 30

Xaa Arg Gly Gly Gly Arg Gly Gly Gly Arg Gly Gly Gly Arg Gly Gly
1               5                   10                  15

Gly Arg Gly Gly Gly Arg Gly Gly Gly Arg
                20                  25
```

TRANSPORTERS COMPRISING SPACED ARGININE MOIETIES

CROSS-REFERENCE TO RELATED APPLICATIONS

This application claims the benefit of U.S. Ser. No. 60/269,627, filed Feb. 16, 2001, the disclosure of which is incorporated by reference herein.

STATEMENT AS TO RIGHTS TO INVENTIONS MADE UNDER FEDERALLY SPONSORED RESEARCH AND DEVELOPMENT

This invention was made with the support of NIH grants numbered CA31841, CA31845, and CA65237. Accordingly, the U.S. Government has certain rights in this invention.

BACKGROUND OF THE INVENTION

There are a number of natural barriers that exist in living organisms. The barriers most likely developed over time as a mechanism to exclude harmful stimuli, such as toxic chemicals, from sensitive biochemical pathways. Cellular membranes, epithelial tissues and endothelial tissues are examples of such barriers.

Unfortunately, barriers such as cellular membranes function by excluding chemical compounds possessing particular physical characteristics rather than by specifically repelling harmful compositions. This can be problematic in the field of drug discovery where one is targeting a biopolymer encased in the barrier. Cellular membranes, for instance, are particularly intractable to highly charged compounds such as polynucleotides. When one administers a highly charged compound (e.g., oligonucleotide) to an organism, its medicinal utility is hindered by its inability to efficiently access its intracellular target.

Researchers have attempted to develop technologies for enhancing the transport of chemical compounds across organismal barriers. For instance, Ryser et al. discusses the use of high molecular weight lysine polymers for increasing the transport of various molecules across cellular membranes. See, Ryser, H. J. P., PCT Pub. No. WO 79/00515 (1979). Frankel et al. reports the conjugation of selected molecules to HIV tat protein, which increased cellular uptake of the molecules. See, Frankel et al, PCT Pub. No. WO 91/09958 (1991). Barsoum discusses the use of the HIV tat sequence RKKRRQRRR in (SEQ ID NO:1) in enhancing cellular membrane transport. See, Barsoum et al., PCT Pub. No. WO 94/04686 (1994). Brugidou et al. report the rapid internalization of a 16 amino acid peptide-cholesterol conjugate derived from the Antennapedia homeodomain by cultured neurons. See, Brugidou, J., et al. *Biochem. Biophys. Res. Comm.* 214 (2):685-693 (1995).

Several methods have also been proposed to enhance the transport of compounds across epithelial tissues. For example, chemical enhancers (Burnette, R. R. In *Developmental Issues and Research Initiatives*; Hadgraft J., Ed., Marcel Dekker: 1989, pp. 247-288) and iontophoresis have been used for the transdermal transport of drugs. These efforts have produced fewer than a dozen drugs for transdermal administration.

More recently, methods and compositions have been described for transporting drugs and macromolecules across biological membranes in which the drug or macromolecule is covalently attached to a transport polymer consisting of from 6 to 25 subunits, at least 50% of which contain a guanidino or amidino side chain. The transport polymers are preferably polyarginine peptides composed of all D-, all L- or mixtures of D- and L-arginine subunits (see PCT/US/10571, WO/52614, published Nov. 26, 1998).

Despite the above, a need exists for new compositions and methods for enhancing the transport of compounds across biological barriers. The present invention fulfills this and other needs.

SUMMARY OF THE INVENTION

The present invention provides compositions and methods for enhancing transport of biologically active compounds across biological membranes and across and into animal epithelial or endothelial tissues. The composition includes a biologically active agent and a transport moiety, either linked covalently by a bond or an optional linking group. The transport moiety includes a structure selected from the group consisting of $(ZYZ)_nZ$, $(ZY)_nZ$, $(ZYY)_nZ$ and $(ZYYY)_nZ$. Subunit "Z" is L-arginine or D-arginine, and subunit "Y" is an amino acid that does not comprise an amidino or guanidino moiety. Subscript "n" is an integer ranging from 2 to 10. The method for enhancing transport involves the administration of the aforementioned composition.

BRIEF DESCRIPTION OF THE DRAWINGS

FIG. 7 illustrates the sixty permutations of aca-spaced arginine heptamers that were prepared and evaluated (results shown in FIG. 8).

DETAILED DESCRIPTION OF THE INVENTION

A. Abbreviations and Definitions

Figure 1:
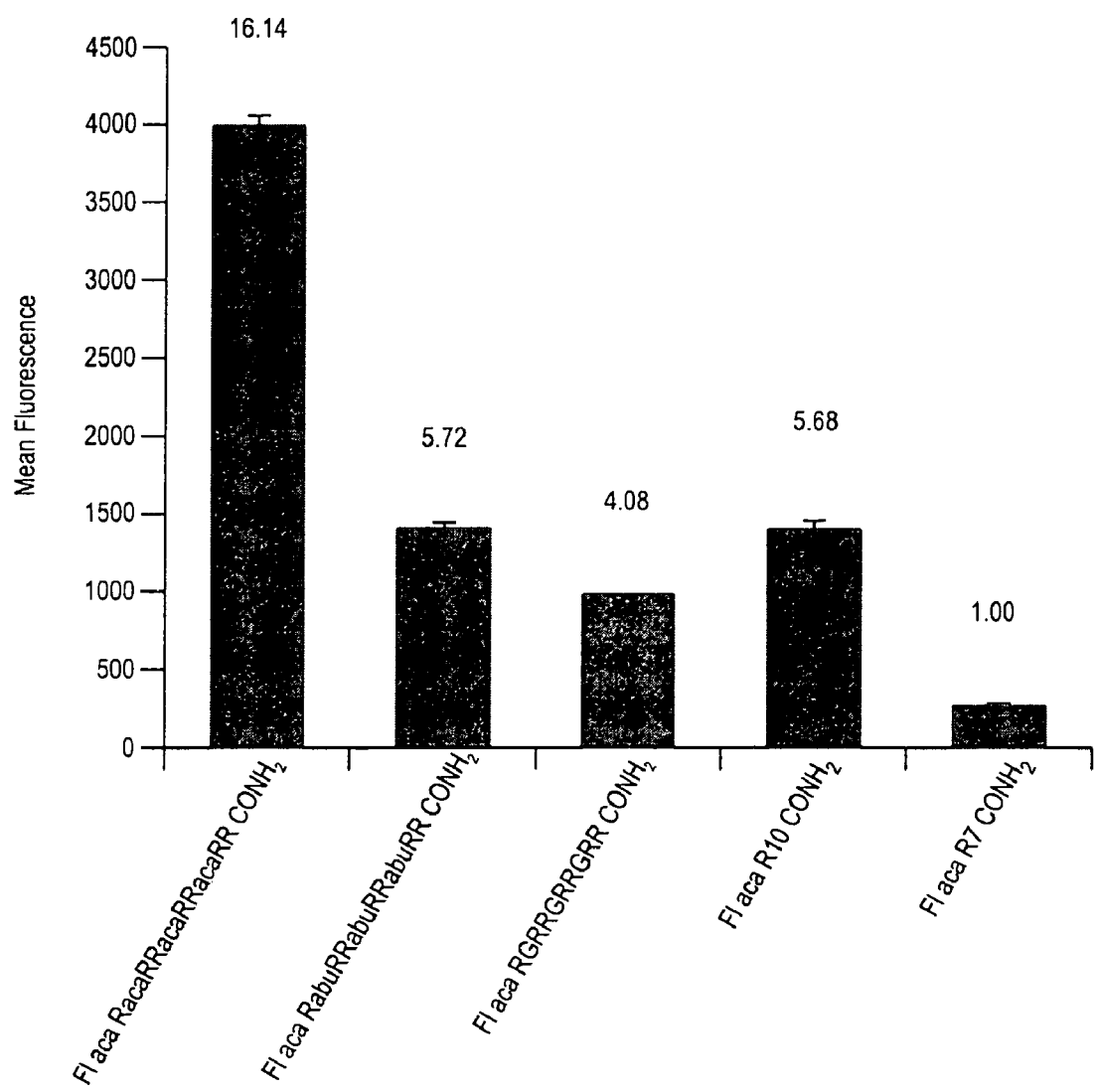
FIG. 1 is a bar graph that illustrates the increase in cellular uptake of a fluorescence agent when a transport oligomer of spaced arginine residues is used relative to the uptake when an R7 homopolymer is the transport oligomer. Uptake increased with increased spacing (glycine insert<aminobutyric acid insert<aminocaproic acid insert).

The following abbreviations are used herein: abu, γ-aminobutyric acid; aca, ε-aminocaproic acid; Fl, fluorescein; Fmoc, fluorenylmethoxycarbonyl. Single letter or three letter abbreviations are used for many amino acid herein in accordance with acceptable convention. Lower case single letter abbreviations for amino acids are intended to denote the D-isomer, also in accordance with conventional use.

The term "alkyl" refers to unsubstituted or substituted linear, branched, cyclic, or combinations of alkyl carbon chains of up to 15 carbon atoms. Linear alkyl groups include, for example, methyl, ethyl, n-propyl, n-butyl, n-pentyl, n-hexyl, n-heptyl and n-octyl. Branched alkyl groups include, for example, iso-propyl, sec-butyl, iso-butyl, tert-butyl and neo-pentyl. Cyclic alkyl groups include, for example, cyclopropyl, cyclobutyl, cyclopentyl and cyclohexyl. Combinations of alkyl groups are also within the scope of the present definition and invention (e.g., cyclopropylmethyl, cyclohexylmethyl, cyclobutylpropyl, and the like). The alkyl groups can also be substituted with one or more substituents, preferably from zero to three substituents. Nonlimiting examples of such substituents include $NH_2$, $SH$, $NO_2$, $ONO_2$, $F$, $Cl$, $Br$, $I$, $OH$, $CO_2H$, $CO_2CH_3$, $CN$, alkoxy, alkylthio, alkylamino, dialkylamino, aryl and heteroaryl.

The term "aryl" refers to an unsubstituted or substituted aromatic, carbocyclic group. Aryl groups are either single ring or multiple condensed ring compounds. A phenyl group, for example, is a single ring, aryl group. An aryl group with multiple condensed rings is exemplified by a naphthyl group. Aryl groups can be substituted with one or more substituents, preferably from zero to three substitutents. Nonlimiting examples of such substituents include $NH_2$, $SH$, $NO_2$, $ONO_2$, $F$, $Cl$, $Br$, $I$, $OH$, $CO_2H$, $CO_2CH_3$, $CN$, alkoxy, alkylthio, alkylamino, dialkylamino, aryl and heteroaryl.

The term "heteroaryl" refers to those aryl groups in which one or more heteroatoms (e.g., O, S, N) occupies a position held by a carbon atom or pair of carbon atoms. Examples of suitable heteroaryl groups include pyridine, thiophene, oxazole, benzimidazole, pyrrole, furan, quinoline, quinazoline, and the like.

An "epithelial tissue" refers to the basic tissue that covers surface areas of the surface, spaces, and cavities of the body. Epithelial tissues are composed primarily of epithelial cells that are attached to one another and rest on an extracellular matrix (basement membrane) that is typically produced by the cells. Epithelial tissues include three general types based on cell shape: squamous, cuboidal, and columnar epithelium. Squamous epithelium, which lines lungs and blood vessels, is made up of flat cells. Cuboidal epithelium lines kidney tubules and is composed of cube shaped cells, while columnar epithelium cells line the digestive tract and have a columnar appearance. Epithelial tissues can also be classified based on the number of cell layers in the tissue. For example, a simple epithelial tissue is composed of a single layer of cells, each of which sits on the basement membrane. A "stratified" epithelial tissue is composed of several cells stacked upon one another; not all cells contact the basement membrane. A "pseudostratified" epithelial tissue has cells that, although all contact the basement membrane, appear to be stratified because the nuclei are at various levels.

The term "trans-epithelial" delivery or administration refers to the delivery or administration of agents by permeation through and/or into one or more layers of a body surface or tissue, such as intact skin or a mucous membrane, by topical administration. Thus, the term is intended to include both transdermal (e.g., percutaneous adsorption, and including intradermal) and transmucosal administration. Delivery can be to a deeper layer of the tissue, for example, and/or delivery to the bloodstream.

"Transport enhancement," refers to an increase in amount and/or rate of delivery of a biologically active compound across a biological barrier. The term is also meant to include altering tissue distribution, localization and release of a biologically active compound or agent. The amount of transport enhancement is determined by comparing the delivery of the compound or agent that is not attached to a transport moiety to the delivery of one that is.

"Biological barrier" refers to a physiological barrier to the delivery of a biologically active compound to its intended target site. It includes, for example, biological membranes, epithelial tissue and endothelial tissue.

"Biological membrane" refers to a lipid-containing barrier that separates cells or groups of cells from extracellular space.

"Biologically active compound" refers to a therapeutic compound or a diagnostic agent, as well as lead compounds in a research and development setting. Still further the term is meant to include various probes (e.g., oligonucleotides alone or those having attached imaging agents).

The term "therapeutic compound" refers, without limitation, to any composition that can be used to the benefit of a mammalian species. A number of such agents cause an observable change in the structure, function or composition of a cell upon uptake by the cell. Observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased rate of synthesis of a metabolite, increased or decreased cell proliferation and the like. Other agents exert therapeutic effects when present in a tissue, even in the absence of cellular entry.

The term "diagnostic agent" refers to both diagnostic imaging agents and contrast agents. The following are non-limiting examples of diagnostic agents: radio-labeled substances such as $^{99}$mTc glucoheptonate; substances used in magnetic resonance imaging such as gadolinium doped chelation agents (e.g., Gd-DTPA); metals bound to chelating agents such as Eu, Lu, Pr, Gd, Tc$^{99}$m, Ga$^{67}$, In$^{111}$, Y$^{90}$, Cu$^{67}$ and Co$^{57}$; and, proteins such as β-galactosidase, green fluorescent protein and luciferase. Other diagnostic agents include molecular sensors.

The term "macromolecule" refers to large molecules (MW greater than 1000 daltons) exemplified by, but not limited to, peptides, proteins, oligonucleotides and polynucleotides of biological or synthetic origin.

"Small organic molecule" refers to a carbon-containing agent having a molecular weight (MW) of less than or equal to 1000 daltons.

The term "peptide" refers to a compound made up of a single chain of D- or L-amino acids or a mixture of D- and L-amino acids joined by peptide bonds. Generally, peptides contain at least two amino acid residues and are less than about 50 amino acids in length. D-amino acids are represented herein by a lower-case one-letter amino acid symbol (e.g., r for D-arginine), whereas L-amino acids are represented by an upper case one-letter amino acid symbol (e.g., R for L-arginine). Homopolymer peptides are represented by a one-letter amino acid symbol followed by the number of consecutive occurrences of that amino acid in the peptide— (e.g., R7 represents a heptamer that consists of L-arginine residues).

The term "protein" refers to a compound that is composed of linearly arranged amino acids linked by peptide bonds, but in contrast to peptides, has a well-defined conformation. Proteins, as opposed to peptides, generally consist of chains of 50 or more amino acids.

"Polypeptide" refers to a oligomer of at least two amino acid residues and which contains one or more peptide bonds. "Polypeptide" encompasses peptides and proteins, regardless of whether the polypeptide has a well-defined conformation.

The term "half-life" generally refers to the time required for half the quantity of a compound to be destroyed, degraded or eliminated. In the context of self-immolating linkers, "half-life" refers to the time required for half the quantity of a transport moiety-biologically active compound conjugate containing such a linker to undergo intramolecular cleavage.

B. General

The present invention relates to the surprising discovery that arginine residues provide an enhanced transport of drugs and other agents across biological membranes when the residues are part of a polypeptide that provides suitable spacing between the arginines. This is in contrast to the previously described polymers of, for example, arginine, in which the guanidino moieties are present on essentially all subunits of the transport polymer. Thus, the transport oligomers of the present invention can be viewed in one group of embodiments as polypeptides in which arginine residues are present, but separated by other amino acids such that, at most, two arginine residues are adjacent. Additionally, the remaining amino acids residues can be selected to provide side chains that enhance solubility and which do not encumber the conformational freedom of the transport oligomer. Alternatively, one of the remaining amino acids can provide a site for attachment to either a linking group or the therapeutic agent of interest (e.g., a serine hydroxyl group, a lysine amino group or a cysteine thiol).

C. Transport Moiety—Biologically Active Compound Conjugates

As noted above, the present invention provides compositions and methods that enhance the transport of biologically active compounds across biological membranes and across and into animal epithelial or endothelial tissue. The compositions are represented by the formula $R^1$—L—$R^3$, wherein $R^1$ is a biologically active compound (i.e., a therapeutic compound, diagnostic agent, lead compound or a probe), $R^3$ is a transport moiety and "L" is an optional linking moiety.

The transport moieties are amino acid oligomers of the following formulae: $(ZYZ)_nZ$, $(ZY)_nZ$, $(ZYY)_nZ$ and $(ZYYY)_nZ$. "Z" in the formulae is D or L-arginine. "Y" is an amino acid that does not contain a guanidyl or amidinyl moiety. The subscript "n" is an integer ranging from 2 to 25.

In the above transport moiety formulae, the letter "Y" represents a natural or non-natural amino acid. The amino acid can be essentially any compound having prior to incorporation into the transport moiety) an amino group ($NH_2$ or NH-alkyl) and a carboxylic acid group ($CO_2H$) and not containing either a guanidyl or amidinyl moiety. Examples of such compounds include D and L-alanine, D and L-cysteine, D and L-aspartic acid, D and L-glutamic acid, D and L-phenylalanine, glycine, D and L-histidine, D and L-isoleucine, D and L-lysine, D and L-leucine, D and L-methionine, D and L-asparagine, D and L-proline, D and L-glutamine, D and L-serine, D and L-threonine, D and L-valine, D and L-tryptophan, D and L-hydroxyproline, D and L-tyrosine, sarcosine, β-alanine, γ-amino butyric acid and ε-amino caproic acid. In each of the above formulae, each Y will be independent of any other Y present in the transport moiety, though in some embodiments, all Y groups can be the same.

In one group of preferred embodiments, the transport moiety has the formula $(ZYZ)_nZ$, wherein each "Y" is independently selected from glycine, β-alanine, γ-amino butyric acid and ε-amino caproic acid, "Z" is preferably L-arginine, and n is preferably an integer ranging from 2 to 5. More preferably, each "Y" is glycine or ε-amino caproic acid and n is 3. Within this group of embodiments, the use of glycine is preferred for those compositions in which the transport moiety is fused or covalently attached directly to a polypeptide biological agent such that the entire composition can be prepared by recombinant methods. For those embodiments in which the transport moiety is to be assembled using, for example, solid phase methods, ε-amino caproic acid is preferred.

In another group of preferred embodiments, the transport moiety has the formula $(ZY)_nZ$, wherein each "Y" is preferably selected from glycine, β-alanine, γ-amino butyric acid and ε-amino caproic acid, "Z" is preferably L-arginine, and n is preferably an integer ranging from 4 to 10. More preferably, each "Y" is glycine or ε-amino caproic acid and n is 6. As with the above group of specific embodiments, the use of glycine is preferred for those compositions in which the transport moiety is fused or covalently attached directly to a polypeptide biological agent such that the entire composition can be prepared by recombinant methods. For solution or solid phase construction of the transport moiety, ε-amino caproic acid is preferred.

In yet another group of preferred embodiments, the transport moiety has the formula $(ZYY)_nZ$, wherein each "Y" is preferably selected from glycine, β-alanine, γ-amino butyric acid and ε-amino caproic acid, "Z" is preferably L-arginine, and n is preferably an integer ranging from 4 to 10. More preferably, each "Y" is glycine or ε-amino caproic acid and n is 6.

In still another group of preferred embodiments, the transport moiety has the formula $(ZYYY)_nZ$, wherein each "Y" is preferably selected from glycine, β-alanine, γ-amino butyric acid and ε-amino caproic acid, "Z" is preferably L-arginine, and n is preferably an integer ranging from 4 to 10. More preferably, "Y" is glycine and n is 6.

In other embodiments, each of the Y groups will be selected to enhance certain desired properties of the transport moiety. For example, when transport moeities having a more hydrophobic character are desired, each Y can be selected from those naturally occurring amino acids that are typically grouped together as hydrophobic amino acids (e.g., phenylalanine, phenylglycine, valine, leucine, isoleucine). Similarly, transport moieties having a more hydrophilic character can be prepared when some or all of the Y groups are hydrophilic amino acids (e.g., lysine, serine, threonine, glutamic acid, and the like).

One of skill in the art will appreciate that the transport moiety can be a polypeptide fragment within a larger polypeptide. For example, the transport moiety can be of the formula $(ZYY)_nZ$ yet have additional amino acids which flank this moiety (e.g., $X_m(ZYY)_nZ$—$X_p$ wherein the subscripts m and p represent integers of zero to about 10 and each X is independently a natural or non-natural amino acid).

Thus, the transport moiety can be viewed as a peptide or having certain peptide character in the sense that it has a carboxy terminus and an amino terminus. One of the termini is either covalently attached to a biologically active compound ($R^1$) or, alternatively, to a linking moiety (L) that is part of a linking moiety-active compound conjugate (e.g., $R^1$—L). For those embodiments in which the transport moiety is covalently attached directly to a biologically active compound, the point of attachment is preferably the carboxy terminus. For those embodiments in which the transport moiety is covalently attached to a linking moiety, the point of attachment is preferably the amino terminus. In still other embodiments, the biologically active compound can be attached to the transport moiety via a linking moiety that is in turn attached to an amino acid side chain functional group (e.g., the hydroxy group of a serine residue, the amino group of a lysine residue, the carboxylic acid group of a glutamic acid residue, and the like).

Turning next to the biologically active compound ($R^1$), the present invention finds broad application to essentially any therapeutic or diagnostic agent. Examples of therapeutic compounds include, without limitation, the following: topical antipsoriasis drugs such as corticosteroids, calcipotriene and anthralin; photochemotherapeutic agents such as psoralens; phorphyrins and enlarged phorphyrins; sunscreen components such as p-aminobenzoic esters, cinnamates, salicylates, benzophenones, anthranilates and avobenzone; pain relief agents and local anesthetics such as lidocaine, novocaine, procaine, tetracaine, benzocaine, cocaine and the opiates; biological agents such as minoxidil, keratolytic agents; destructive agents such as podophyllin, hydroquinone, masoprocol, colchicine and gold; drugs for gastrointestinal conditions such as cyclosporin, FK506, $H_2$ histamine inhibitors (e.g., cymetidine and ranitidine), ATPase proton-potassium inhibitors (e.g., lansoprazole and omeprazle); antiobiotics such as norfloxacin, ciprofloxacin, trimethoprim and sulfamethyloxazole; antineoplastic agents such as cisplatin, methotrexate, taxol, flurouracil, mercaptopurine, donorubicin and bleomycin; antiinflammatory agents such as corticosteroids, cromolyn and nedocromil; immunosuppressive drugs such as cyclosporin and FK506; drugs acting on pulmonary tissues such as beta-agonists, mast cell stabilizers, antibiotics, antifungal agents, antiviral agents, vasoactive drugs, sedatives and hormones; CNS agents such as anti-apoptotics, neurotransmitters, morphine, opiates and 5-hydroxy-tryptamine receptor antagonists; small molecules such as L-3,4-dihydroxy phenylalanine (L-DOPA; taxanes such as paclitaxel; proteins such as alglucerase, alpha-L-iduronidase, alpha-N-acetylglucosamidase, lipase, adenosine deaminase and triose phosphate isomerase; peptides having phosphorylation sites used by proteins mediating intracellular signals such as protein kinase C, RAF-1, p21Ras, NF-κB and C-JUN; cytoplasmic tails of membrane receptors such as IL-4 receptor, CD28, CTLA-4, V7, MHC Class I antigens and MHC Class II antigens; oligonucleotides and polynucleotides formed of DNA and RNA; oligonucleotide analogs such as phosphonates (e.g., methyl phosphonates), phosphoramidates (N3' or N5'), thiophosphates, uncharged morpholino-based polymers and protein nucleic acids (PNAs); and, polysaccharides and polysaccharide analogs.

Diagnostic agents include both diagnostic imaging agents and contrast agents. The following are non-limiting examples of diagnostic agents: radio-labeled substances such as $^{99}$mTc glucoheptonate; substances used in magnetic resonance imaging such as gadolinium doped chelation agents (e.g., Gd-DTPA); metals bound to chelating agents such as Eu, Lu, Pr, Gd, Tc$^{99}$m, Ga$^{67}$, In$^{111}$, Y$^{90}$, Cu$^{67}$ and Co$^{57}$; and, proteins such as β-galactosidase, green fluorescent protein and luciferase. Still other useful agents include dyes such as, for example, fluorescein.

In certain embodiments, the transport moiety is attached to the biologically active compound through a linking moiety (L). Such a linking moiety has two termini, one that covalently bonds to the transport moiety and one that covalently bonds to the biologically active compound. The termini each contain a functional group that serves as a facile point of attachment. Examples of such groups include, without limitation, carboxylic acids, carboxylic acid derivatives, alcohols, amines and thiols. For example, $HO_2CCH_2CH_2OH$ is a linking moiety having a carboxylic acid at one terminus and an alcohol at the other. One formula representing its use in attaching the transport moiety to the biologically active compound is as follows: $R^1$—$O_2CCH_2CH_2O$—$R^3$.

The linking moiety is preferably cleaved in vivo. "Cleaved" in this case refers to separation of a linking moiety terminus from the biologically active agent. The separation is effected through dissociation of a covalent bond. For instance, where a carboxylic acid terminus of a linking moiety is attached to an alcohol functionality on a biologically active agent (i.e., ester linkage), cleavage results in the formation of a carboxylic acid (linking moiety terminus) and a free active agent.

In one embodiment, the linking moiety is cleaved through hydrolysis. Such hydrolytic cleavages are typically pH dependent. For instance, an acid mediated hydrolysis occurs at a faster rate at pH 6.0 than at pH 7.4.

In another embodiment, the linking moiety is cleaved through self-immolation. Such linking moieties in a transport moiety-biologically active compound conjugate contain a nucleophile (e.g., oxygen, nitrogen and sulfur) distal to the biologically active compound and a cleavable group (e.g., ester, carbonate, carbamate and thiocarbamate) proximal to the biologically active compound. Intramolecular attack of the nucleophile on the cleavable group results in the scission of a covalent bond, thereby releasing the linking moiety from the biologically active compound.

Examples of conjugates containing self-immolating linking moieties (e.g., biologically active agent-L-transport moiety conjugates) are represented by structures 1, 2 and 3:

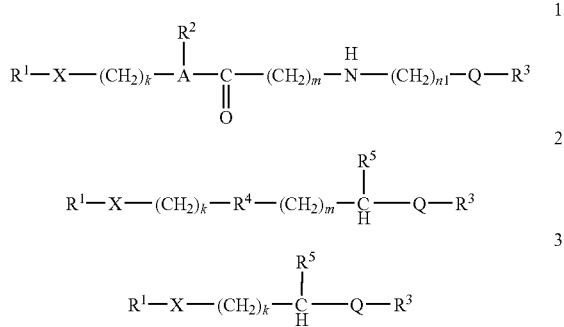

wherein: $R^1$ is the biologically active compound; X is a linkage formed between a functional group on the biologically active compound and a terminal functional group on the linking moiety; Q is a linkage formed from a functional group on the transport moiety and a functional group on the linking moiety; A is N or CH; $R^2$ is hydrogen, alkyl, aryl, arylalkyl, acyl or allyl; $R^3$ is the transport moiety; $R^4$ is S, O, $NR^6$ or $CR^7R^8$; $R^5$ is H, OH, SH or $NHR^6$; $R^6$ is hydrogen, alkyl, aryl, acyl or allyl; $R^7$ and $R^8$ are independently hydrogen or alkyl; k and m are independently either 1 or 2; and n1 is an integer ranging from 1 to 10. Non-limiting examples of the X and Q linkages are (in either orientation): —C(O)O—, —C(O)NH—, —OC(O)NH—, —S—S—, —C(S)O—, —C(S)NH—, —NHC(O)NH—, —SO$_2$NH—, —SONH—, phosphate, phosphonate and phosphinate. One of skill in the art will appreciate that when the biological agent has a hydroxy functional group, then X will preferably be —OC(O)— or —OC(O)NH—. Similarly, when the linking group is attached to an amino terminus of the transport moiety, Q will preferably be —C(O)NH—, —NHC(O)NH—, —SO$_2$NH—, —SONH— or —OC(O)NH— and the like. In each of the groups provided above, NH is shown for brevity, but each of the linkages (X and Q) can contain substituted (e.g., N-alkyl or N-acyl) linkages as well.

Turning first to linking groups illustrated by structure 1, an example and preferred embodiment is illustrated for formula 1a:

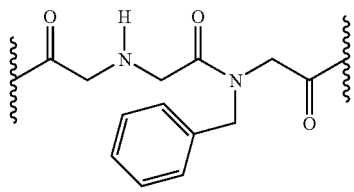

1a wherein the wavy lines indicate points of attachment to the transport moiety and to the biologically active compound. Preparation of a conjugate containing this linking group is illustrated in Example 4 (FIG. 9). In this Example and FIG. 9, cyclosporin A is treated with chloroacetic anhydride to form the chloroacetate ester 9i (numbering in FIG. 9) which is then combined with benzylamine to form the N-benzyl glycine conjugate 9ii. Condensation of the glycine conjugate with Boc-protected diglycine anhydride provides the acid 9iii which is converted to the more reactive N-hydroxy succinimide ester 9iv and then combined with the amino terminus of a transport moiety to form an amide linkage. One of skill in the art will appreciate that the N-benzyl group can be replaced with other groups (e.g., alkyl, aryl, allyl and the like) or that methylene groups can be replaced with, for example, ethylene, propylene and the like. Preferably, the methylene groups are retained as shown in 1a, to provide an appropriate steric or spatial orientation which allows the linkage to be cleaved in vivo (see FIG. 9B).

Accordingly, for structure 1, the following substituents are preferred: A is N; $R^2$ is benzyl; k, m and n1 are 1; X is —OC(O)— and Q is —C(O)NH—.

Linkages of structure 2, are exemplified by formula 2a:

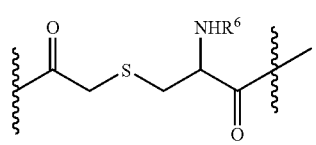

Figure 10:
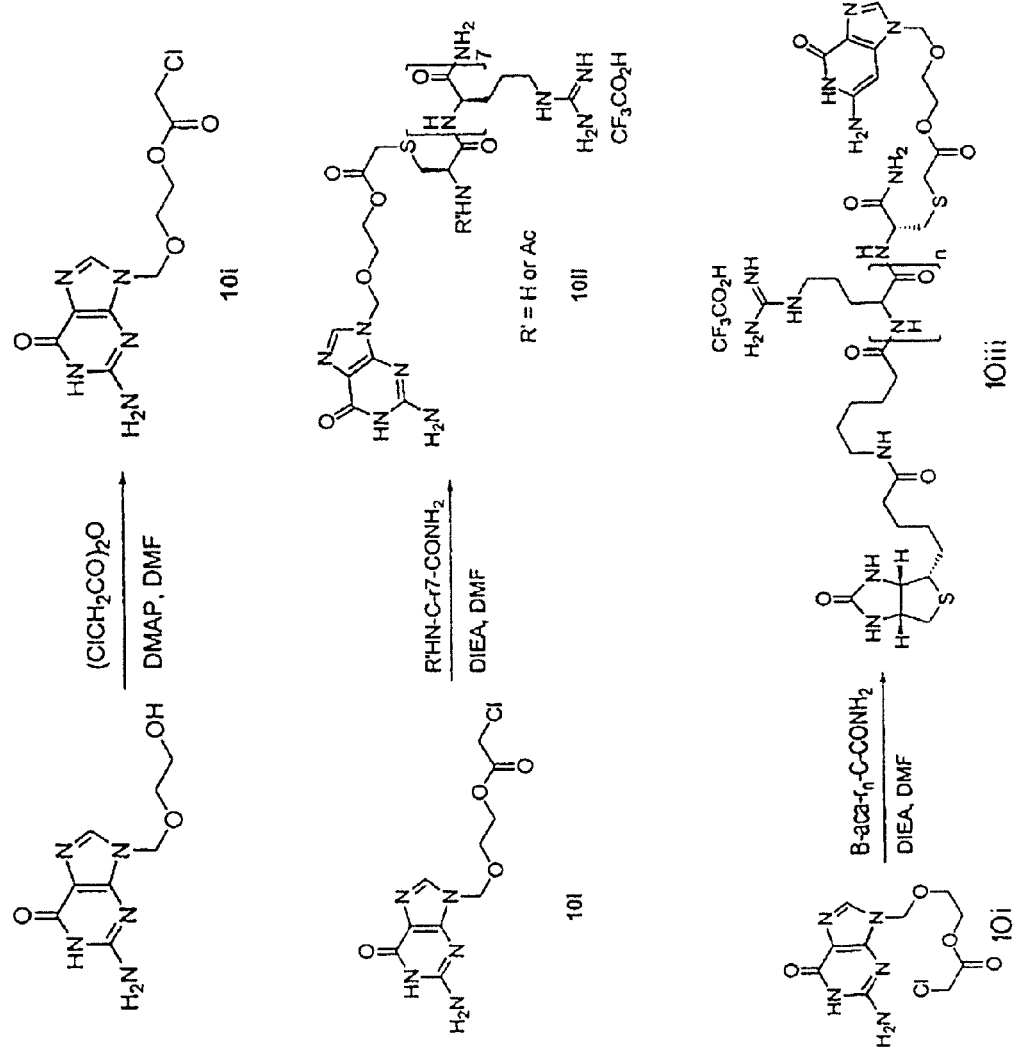
FIG. 10 illustrates the conjugation of acyclovir to r7-amide via an N-terminal cysteine group. Conjugation with a biotin-containing transporter is also shown.
Figure 11:
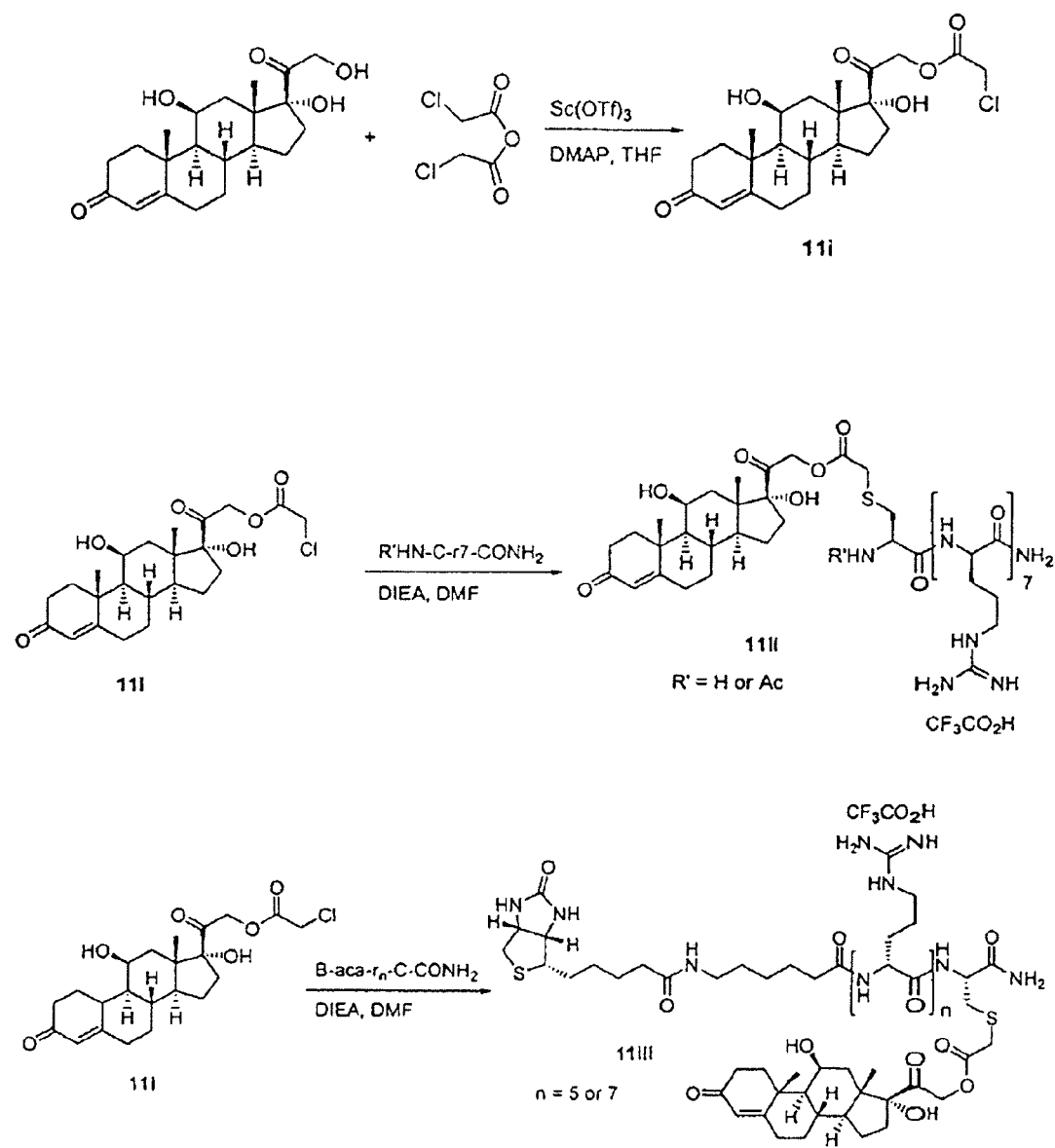
FIG. 11 illustrates the conjugation of hydrocortisone to r7-amide via an N-terminal cysteine group. Conjugation with a biotin-containing transporter is also shown.

2a wherein, as above, the wavy lines indicate the point of attachment to each of the transport moiety and the biologically active agent. The preparation of conjugates having linking groups of formula 2a are shown in Examples 5-7. In Example 5 (see scheme in FIG. 10), acyclovir is acylated with α-chloroacetic anhydride to form the α-chloroacetate ester 10i. Reaction of 10i with a heptamer of D-arginine having an N-terminal cysteine residue, provides the thioether product 10ii. Alternatively, acyclovir can be attached to the C-terminus of a transport moiety (see Example 5b) using a similar linkage formed between acyclovir α-chloroacetate ester and a heptamer of D-arginine having an C-terminal cysteine residue. In this instance, the cysteine residue is provided on the $r_7$ transport moiety as a C-terminal amide and the linkage has the form:

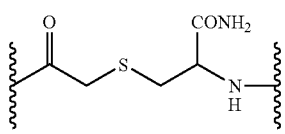

Accordingly, in one group of preferred embodiments, the conjugate is represented by formula 2, in which X is —OC(O)—; Q is —C(O)NH—; $R^4$ is S; $R^5$ is $NHR^6$; and the subscripts k and m are each 1. In another group of preferred embodiments, the conjugate is represented by formula 2, in which X is —OC(O)—; Q is —NHC(O)—; $R^4$ is S; $R^5$ is CONH$_2$; and the subscripts k and m are each 1. Particularly preferred conjugates are those in which $R^6$ is hydrogen, methyl, allyl, butyl or phenyl.

Linking groups represented by the conjugates shown in formula 3 are generally of the heterobifunctional type (e.g., ε-aminocaproic acid, serine, homoserine, γ-aminobutyric acid, and the like), although suitably protected dicarboxylic acids or diamines are also useful with certain biological agents.

For structure 3, the following substituents are preferred: $R^5$ is $NHR^6$, wherein $R^6$ is hydrogen, methyl, allyl, butyl or phenyl; k is 2; X is —C(O)O—; and Q is —C(O)NH—.

Self-immolating linkers typically undergo intramolecular cleavage with a half-life between about 10 minutes and about 24 hours in water at 37° C. at a pH of approximately 7.4. Preferably, the cleavage half-life is between about 20 minutes and about 4 hours in water at 37° C. at a pH of approximately 7.4. More preferably, the cleavage half-life is between about 30 minutes and about 2 hours in water at 37° C. at a pH of approximately 7.4.

For a conjugate having the structure 1, one can adjust the cleavage half-life by varying the $R^2$ substituent. By using an $R^2$ of increased or decreased size, one can obtain a conjugate having a longer or shorter half-life respectively. $R^2$ in structure 1 is preferably methyl, ethyl, propyl, butyl, allyl, benzyl or phenyl.

Where there is a basic or acidic group in a self-immolating linker, one can oftentimes adjust cleavage half-life according to the pH of the conjugate solution. For instance, the backbone amine group of structure 1 is protonated at acidic pH (e.g., pH 5.5). The amine cannot serve as a nucleophile inducing intramolecular cleavage when it is protonated. Upon introduction of the conjugate into a medium at physiological pH (7.4), however, the amine is unprotonated a significant portion of the time. The cleavage half-life is correspondingly reduced.

In one embodiment, cleavage of a self-immolating linker occurs in two steps: intramolecular reaction of a nucleophilic group resulting in the cleavage of a portion of the linking moiety; and, elimination of the remaining portion of the linking moiety. The first step of the cleavage is rate-limiting and can be fine-tuned for pH sensitivity and half-life.

Structure 4 is an example of a two-step, self-immolating moiety that is incorporated into a transport moiety-biologically active compound conjugate:

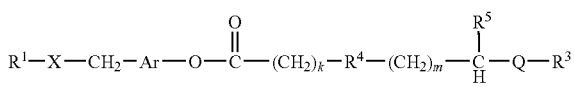

4 wherein: $R^1$ is the biologically active compound; X represents a linkage between a functional group on the biologically active compound and a functional group on the linking moiety; Ar is a substituted or unsubstituted aryl group, wherein the methylene substituent and phenolic oxygen atom are either ortho or para to one another; $R^3$ is the transport moiety; $R^4$ is S, O, $NR^6$ or $CR^7R^8$; $R^5$ is H, OH, SH or $NHR^6$; $R^6$ is hydrogen, alkyl, aryl, arylalkyl, acyl or allyl; $R^7$ and $R^8$ are independently hydrogen or alkyl; and, k and m are independently either 1 or 2.

An example of a suitable linking group to produce a conjugate of formula 4 is:

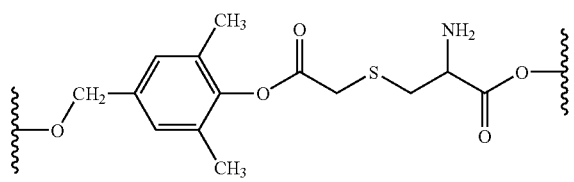

4a

Figure 14:
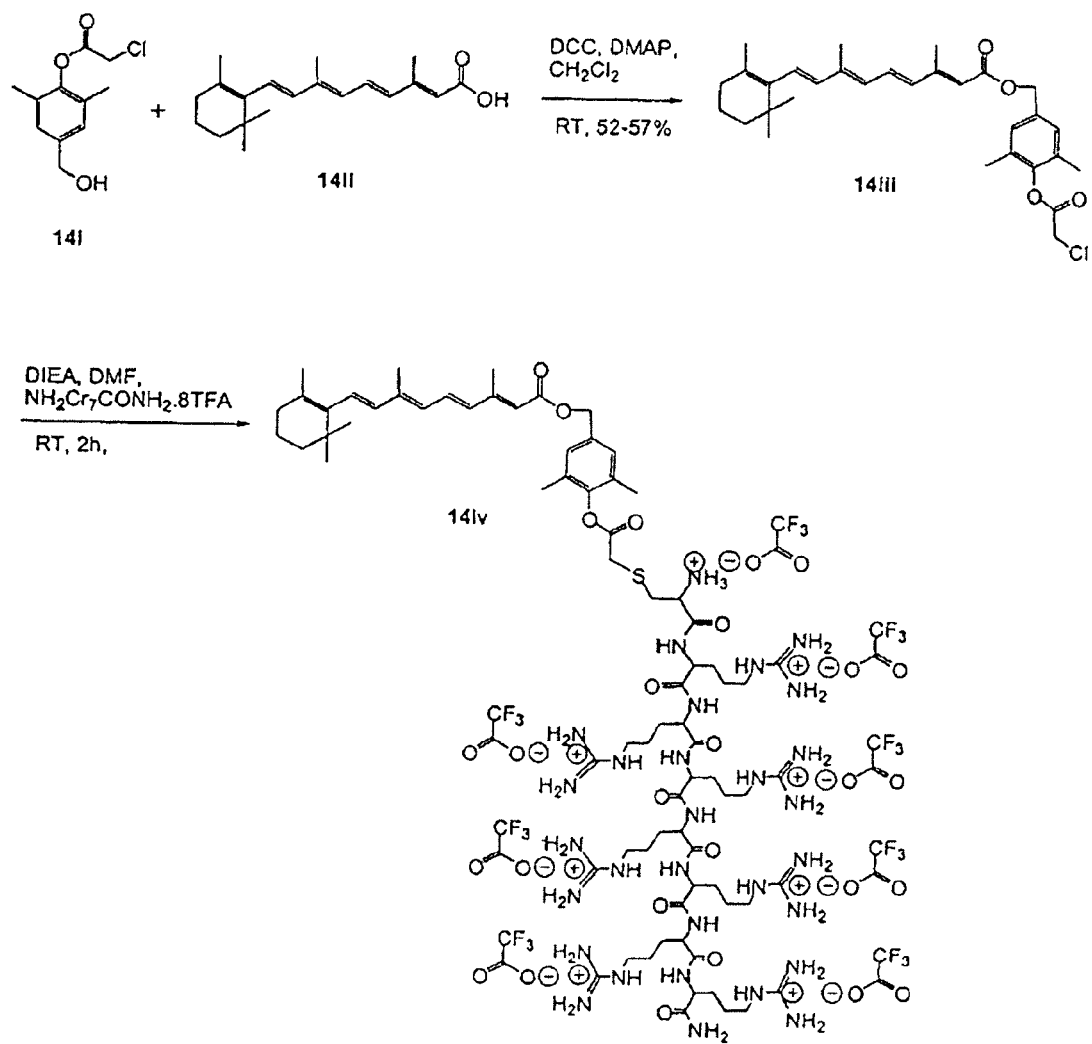
FIG. 14 illustrates the use of a cleavable linker in preparing a retinoic acid-r9 conjugate.

The construction of a conjugate containing a linking group of formula 4a is provided in Example 8 (see also FIG. 14). In this example (and Figure), the α-chloroacetate ester of 2,4-dimethyl-4-hydroxymethylphenol (14i) is coupled to retinoic acid (14ii) using dicyclohexylcarbodiimide (DCC) and 4-dimethylaminopyridine (DMAP) to provide the intermediate 14iii. Subsequent coupling of 14iii with a cysteine residue present on the N-terminus of an arginine heptamer transport moiety provides the target conjugate 14iv.

Preferably, the linking groups used in the conjugates of formula 4, are those in which Ar is an substituted or unsubstituted phenylene group; $R^4$ is S; $R^5$ is $NHR^6$, wherein $R^6$ is hydrogen, methyl, allyl, butyl, acetyl or phenyl; k and m are 1; X is —C(O)O—; and Y is —C(O)O— or —C(O)NH—. More preferably, $R^6$ is hydrogen or acetyl.

While linking groups above have been described with reference to conjugates containing arginine heptamers, one of skill in the art will understand that the technology is readily adapted to conjugates with the "spaced" arginine transport moieties of the present invention.

Still other useful linking groups for use in the present invention have been described in copending PCT applications. See, for example PCT applications US98/10571 (Publication No. WO 9852614) and US00/23440 (Publication No. WO 01/13957) which describe linking groups for similar compositions, e.g., conjugates of biologically active agents and transport oligomers. The linking technology described therein can be used in the present compositions in a similar manner.

Thus, in one group of embodiments, the linking moiety contains a first cleavable group distal to the biologically active compound and a second cleavable group proximal to the biologically active compound. Cleavage of the first cleavable group yields a nucleophile capable of reacting intramolecularly with the second cleavable group, thereby cleaving the linking moiety from the biologically active compound. Examples of methods by which the first group is cleaved include photo-illumination and enzyme mediated hydrolysis. This methodology has been illustrated for various related small molecule conjugates discussed in PCT application US98/10571 (Publication No. WO 9852614).

In one approach, the conjugate can include a disulfide linkage, as illustrated in FIG. 5A of PCT application US00/23440 (Publication No. WO 01/13957), (see also, PCT application US98/10571 (Publication No. WO 9852614)), which shows a conjugate (I) containing a transport polymer T which is linked to a cytotoxic agent, 6-mercaptopurine, by an N-acetyl-protected cysteine group which serves as a linker. Thus, the cytotoxic agent is attached by a disulfide bond to the 6-mercapto group, and the transport polymer is bound to the cysteine carbonyl moiety via an amide linkage. Cleavage of the disulfide bond by reduction or disulfide exchange results in release of the free cytotoxic agent. A method for synthesizing a disulfide-containing conjugate is provided in Example 9A of PCT application US98/10571. The product described therein contains a heptamer of Arg residues which is linked to 6-mercaptopurine by an N-acetyl-Cys-Ala-Ala linker, where the Ala residues are included as an additional spacer to render the disulfide more accessible to thiols and reducing agents for cleavage within a cell. The linker in this example also illustrates the use of amide bonds, which can be cleaved enzymatically within a cell.

In another approach, the conjugate includes a photocleavable linker which is cleaved upon exposure to electromagnetic radiation. Application of this methodology is provided for a related system in FIG. 5B of PCT application US00/23440 (Publication No. WO 01/13957) which shows a conjugate (II) containing a transport polymer T which is linked to 6-mercaptopurine via a meta-nitrobenzoate linking moiety. Polymer T is linked to the nitrobenzoate moiety by an amide linkage to the benzoate carbonyl group, and the cytotoxic agent is bound via its 6-mercapto group to the p-methylene group. The compound can be formed by reacting 6-mercaptopurine with p-bromomethyl-m-nitrobenzoic acid in the presence of $NaOCH_3$/methanol with heating, followed by coupling of the benzoate carboxylic acid to a transport polymer, such as the amino group of a γ-aminobutyric acid linker attached to the polymer (see also, e.g., Example 9B of PCT application US98/10571). Photo-illumination of the conjugate causes release of the 6-mercaptopurine by virtue of the nitro group that is ortho to the mercaptomethyl moiety. This approach finds utility in phototherapy methods as are known in the art, particularly for localizing drug activation to a selected area of the body.

In one group of preferred embodiments, the cleavable linker contains first and second cleavable groups that can cooperate to cleave the oligomer from the biologically active agent, as illustrated by the following approaches. That is, the cleavable linker contains a first cleavable group that is distal to the agent, and a second cleavable group that is proximal to the agent, such that cleavage of the first cleavable group yields a linker-agent conjugate containing a nucleophilic moiety capable of reacting intramolecularly to cleave the second cleavable group, thereby releasing the agent from the linker and oligomer.

Reference is again made to co-owned and copending PCT application US00/23440 (Publication No. WO 01/13957), in which FIG. 5C shows a conjugate (III) containing a transport polymer T linked to the anticancer agent, 5-fluorouracil (5FU). In that figure, the linkage is provided by a modified lysyl residue. The transport polymer is linked to the α-amino group, and the 5-fluorouracil is linked via the α-carbonyl. The lysyl ε-amino group has been modified to a carbamate ester of o-hydroxymethyl nitrobenzene, which comprises a first, photolabile cleavable group in the conjugate. Photo-illumination severs the nitrobenzene moiety from the conjugate, leaving a carbamate that also rapidly decomposes to give the free α-amino group, an effective nucleophile. Intramolecular reaction of the ε-amino group with the amide linkage to the 5-fluorouracil group leads to cyclization with release of the 5-fluorouracil group.

Still other linkers useful in the present invention are provided in PCT application US00/23440 (Publication No. WO 01/13957). In particular, FIG. 5D of US00/23440 illustrates a conjugate (IV) containing a delivery-enhancing transporter T linked to 2'-oxygen of the anticancer agent, paclitaxel. The linkage is provided by a linking moiety that includes (i) a nitrogen atom attached to the delivery-enhancing transporter, (ii) a phosphate monoester located para to the nitrogen atom, and (iii) a carboxymethyl group meta to the nitrogen atom, which is joined to the 2'-oxygen of paclitaxel by a carboxylate ester linkage. Enzymatic cleavage of the phosphate group from the conjugate affords a free phenol hydroxyl group. This nucleophilic group then reacts intramolecularly with the carboxylate ester to release free paclitaxel, fully capable of binding to its biological target. Example 9C of PCT application US98/10571 describes a synthetic protocol for preparing this type of conjugate.

Still other suitable linkers are illustrated in FIG. 5E of PCT application US00/23440 (Publication No. WO 01/13957). In the approach provided therein, a delivery-enhancing transporter is linked to a biologically active agent, e.g., paclitaxel, by an aminoalkyl carboxylic acid. Preferably, the linker amino group is linked to the linker carboxyl carbon by from 3 to 5 chain atoms (n1=3 to 5), preferably either 3 or 4 chain atoms, which are preferably provided as methylene carbons. As seen in FIG. 5E, the linker amino group is joined to the delivery-enhancing transporter by an amide linkage, and is joined to the paclitaxel moiety by an ester linkage. Enzymatic cleavage of the amide linkage releases the delivery-enhancing transporter and produces a free nucleophilic amino group. The free amino group can then react intramolecularly with the ester group to release the linker from the paclitaxel.

In another approach, the conjugate includes a linker that is labile at one pH but is stable at another pH. For example, FIG. 6 of PCT application US00/23440 (Publication No. WO 01/13957) illustrates a method of synthesizing a conjugate with a linker that is cleaved at physiological pH but is stable at acidic pH. Preferably, the linker is cleaved in water at a pH of from about 6.6 to about 7.6. Preferably the linker is stable in water at a pH from about 4.5 to about 6.5.

D. Synthesis of Transport Moieties and Compositions

The transporters of the present invention can be constructed using a variety of conventional synthetic methods. For example, the amino acid oligomers can be produced synthetically, preferably using a peptide synthesizer (e.g., and Applied Biosystems Model 433) or can be synthesized recombinantly using methods well-known in the art. Recombinant synthesis is generally used when the biologically active compound attached to the transport moiety is a peptide or protein.

In other embodiments, the transport oligomers can be prepared using solid phase peptide synthesis which is extensively described and used in the art to prepare peptides. The transport oligomers can also be prepared using liquid phase synthetic methods, which are also well known in the art. See, M. Bodanszky and A. Bodanszky, The Practice of Peptide Synthesis, 2nd ed., Springer-Verlag, New York, N.Y. (1994).

E. Uses of the Present Invention

The transport moiety-biologically active compound conjugates of the present invention find use in therapeutic, prophylactic and diagnostic applications. The conjugates readily penetrate biological membranes, move across and/or into one or more layers of skin or other epithelial tissue (e.g., gastrointestinal, lung and the like) and traverse endothelial tissues (e.g., blood-brain barrier). This property makes the conjugates useful where transport compounds must penetrate such membranes or tissues to exert their effect.

Conjugates and methods of the present invention have particular utility in the area of human and veterinary therapeutics. Generally, administered dosages will be effective to deliver picomolar to micromolar concentrations of the therapeutic composition to the effector site. Appropriate dosages and concentrations will depend on factors such as the therapeutic composition or drug, the site of intended delivery, and the route of administration, all of which can be derived empirically according to methods well known in the art. Further guidance can be obtained from studies using experimental animal models for evaluating dosage, as are known in the art.

Administration of the conjugates of the invention with a suitable pharmaceutical excipient as necessary can be carried out via any of the accepted modes of administration. Thus, administration can be, for example, intravenous, topical, subcutaneous, transcutaneous, intramuscular, oral, intra-joint, parenteral, peritoneal, intranasal, transocular, sublingual, or by inhalation. Suitable sites of administration thus include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art, e.g., *REMINGTON'S PHARMACEUTICAL SCIENCES*, 18TH ED., Mack Publishing Co., Easton, Pa. (1990).

For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing conjugate (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see *Remington's Pharmaceutical Sciences*, supra., and similar publications. The composition to be administered will, in any event, contain a quantity of the pro-drug and/or active compound(s) in a pharmaceutically effective amount for relief of the condition being treated when administered in accordance with the teachings of this invention.

Generally, the conjugates of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

F. Delivery Methods Using the Present Invention

The delivery-enhancing transport moieties of the invention make possible or enhance the delivery of biologically active compounds across the skin. Surprisingly, the transport moieties can deliver an agent across the stratum corneum, which previously had been a nearly impenetrable barrier to drug delivery. The stratum corneum, the outermost layer of the skin, is composed of several layers of dead, keratin-filled skin cells that are tightly bound together by a "glue" composed of cholesterol and fatty acids. Once the agents are delivered through the stratum corneum by the transporters of the invention, the agents can enter the viable epidermis, which is composed of the stratum granulosum, stratum lucidum and stratum germinativum which, along with the stratum corneum, make up the epidermis. Delivery in some embodiments of the invention is through the epidermis and into the dermis, including one or both of the papillary dermis and the reticular dermis.

This ability to obtain penetration of one or more layers of the skin can greatly enhance the efficacy of compounds such as antibacterials, antifungals, antivirals, antiproliferatives, immunosuppressives, vitamins, analgesics, hormones, and the like. Numerous such compounds are known to those of skill in the art (see, e.g., Hardman and Limbird, *Goodman & Gilman's The Pharmacological Basis of Therapeutics*, McGraw-Hill, New York, 1996).

In some embodiments, the biologically active compound is delivered into a blood vessel that is present in the epithelial tissue, thus providing a means for delivery of the agent systemically. Delivery can be either intrafollicular or interfollicular, or both. Pretreatment of the skin is not required for delivery of the conjugates.

The delivery-enhancing transport moieties of the invention are also useful for delivery of conjugated drugs by gastrointestinal administration. Gastrointestinal administration can be used for both systemically active drugs, and for drugs that act in the gastrointestinal epithelium.

The delivery-enhancing transport moieties of the invention can also used to enhance administration of drugs through the respiratory tract. The respiratory tract, which includes the nasal mucosa, hypopharynx, and large and small airway structures, provides a large mucosal surface for drug absorption. The enhanced penetration of the conjugated agents into and across one or more layers of the epithelial tissue that is provided by the delivery-enhancing transport moieties of the invention results in amplification of the advantages that respiratory tract delivery has over other delivery methods. For example, lower doses of an agent are often needed to obtain a desired effect, a local therapeutic effect can occur more rapidly, and systemic therapeutic blood levels of the agent are obtained quickly. Rapid onset of pharmacological activity can result from respiratory tract administration. Moreover, respiratory tract administration generally has relatively few side effects.

The delivery-enhancing transport moieties are also useful for delivering biologically active compounds across the blood brain barrier. The agents are useful for treating ischemia (e.g., using an anti-apoptotic drug), as well as for delivering neurotransmitters and other agents for treating various conditions such as schizophrenia, Parkinson's disease, pain (e.g., morphine, the opiates). The 5-hydroxytryptamine receptor antagonist is useful for treating conditions such as migraine headaches and anxiety.

G. Examples

Example 1

This example illustrates the synthesis of various peptides, including those having attached linking groups which are natural or non-natural amino acids.

Peptides were synthesized using solid phase techniques and commercially available Fmoc amino acids, resins, and reagents (PE Biosystems, Foster City Calif., and Bachem Torrence, Calif.) on a Applied Biosystems 433 peptide synthesizer. Fmoc amino caproic acid and Fmoc amino butyric acid were purchased from NovaBiochem (San Diego, Calif.). Fastmoc cycles were used with O-(7-azabenzotriazol-1-yl)-1,1,3,3-tetramethyluronium hexfluorophosphate (HATU) substituted for HBTU/HOBt as the coupling reagent. The peptides were cleaved from the resin using 96% trifluoroacetic acid, 2% triisopropyl silane, and 2% phenol for 12 hours. The longer reaction times were necessary to completely remove the Pbf protecting groups from the multiple arginines in the peptides. The peptides subsequently were filtered from the resin, precipitated using diethyl ether, purified using C-18 reverse phase columns (Alltech Altima, Chicago, Ill.) and characterized using either electrospray or matrix assisted laser desorption mass spectrometry (Perceptive Biosystems, Boston, Mass.).

Fluorescent analogs were synthesized by coupling fluorescein isothiocyanate (Aldrich Milwaukee, Wis.) to the amino terminus of the peptide while still attached to the resin.

Table 1 provides a number of transport moieties as their fluorescent conjugates that were prepared and evaluated for cellular uptake.

TABLE 1

| Sequence | Seq. I.D. No. |
|---|---|
| Fl-aca-R7CONH$_2$ | 2 |
| Fl-aca-R10CONH$_2$ | 3 |
| Fl-aca-RGRRGRRGRR-CONH$_2$ | 4 |
| Fl-aca-RabuRRabuRRabuRR-CONH$_2$ | 5 |
| Fl-aca-RacaRRacaRRacaRR-CONH$_2$ | 6 |
| Fl-aca-RARRARRARR-CONH$_2$ | 7 |
| Fl-aca-RDRRDRRDRR-CONH$_2$ | 8 |
| Fl-aca-RERRERRERR-CONH$_2$ | 9 |
| Fl-aca-RFRRFRRFRR-CONH$_2$ | 10 |
| Fl-aca-RHRRHRRHRR-CONH$_2$ | 11 |
| Fl-aca-RIRRIRRIRR-CONH$_2$ | 12 |
| Fl-aca-RKRRKRRKRR-CONH$_2$ | 13 |
| Fl-aca-RLRRLRRLRR-CONH$_2$ | 14 |
| Fl-aca-RMRRMRRMRR-CONH$_2$ | 15 |
| Fl-aca-RNRRNRRNRR-CONH$_2$ | 16 |
| Fl-aca-RPRRPRRPRR-CONH$_2$ | 17 |
| Fl-aca-RQRRQRRQRR-CONH$_2$ | 18 |
| Fl-aca-RSRRSRRSRR-CONH$_2$ | 19 |
| Fl-aca-RTRRTRRTRR-CONH$_2$ | 20 |
| Fl-aca-RVRRVRRVRR-CONH$_2$ | 21 |
| Fl-aca-RYRRYRRYRR-CONH$_2$ | 22 |
| Fl-aca-(Raca)$_4$R-CONH$_2$ | 23 |
| Fl-aca-(Raca)$_5$R-CONH$_2$ | 24 |
| Fl-aca-(Raca)$_6$R-CONH$_2$ | 25 |
| Fl-aca-(RGG)$_6$R-CONH$_2$ | 26 |
| Fl-aca-(RG)$_6$R-CONH$_2$ | 27 |
| r13 | 28 |
| r19 | 29 |
| Fl-aca-(RGGG)$_6$R-CONH$_2$ | 30 |

Example 2

This example illustrates a cellular uptake assay which can be used to evaluate the conjugates of the present invention.

The fluorescently labeled peptides were dissolved in PBS, pH 7.2, and their concentrations were determined by absorption of fluorescein at 490 nm ($\epsilon$=67,000). The human T cell line, Jurkat, grown in 10% fetal calf serum in DMEM, was used for all the cellular uptake experiments. Varying amounts of the peptides were added to 3×10$^5$ cells in a total of 200λ, in wells of microtiter plates, and incubated for varying periods of time, ranging from three to five minutes. The cells were spun, washed three times with cold PBS, incubated with 0.05% trypsin/0.53 mM EDTA (Gibco, Grand Island, N.Y.) at 37° C. for five minutes, washed with PBS, and resuspended in PBS containing 0.1% propidium iodide. The cells were analyzed either using confocal microscopy or fluorescent flow cytometry (FACScan, Becton Dickinson, Milpitas, Calif.). Cells staining with propidium iodide were excluded from the analysis. Data presented is the mean fluorescent signal for the 5000 cells collected. To prevent cellular uptake of the peptides, the cells were treated with sodium azide (1.0%) for 25 minutes prior to exposure to the peptides. Intracellular staining was calculated by subtracting the signal seen on cells treated with sodium azide from that observed on untreated cells.

Example 3

This example provides results of arginine spacing in the cellular uptake assay of Example 2.

3A—Comparison of R7 Homopolymer with Single Amino Acid Spacing (No Side Chains)

A series of arginine containing conjugates was prepared as described in Example 1 and evaluated as described in Example 2. Spacing between seven arginine residues was provided by glycine (see Seq. I.D. No. 4), γ-aminobutyric acid (see Seq. I.D. No. 5), and ε-aminocaproic acid (see Seq. I.D. No. 6). FIG. 1 shows the results of cellular uptake for the "spaced" arginine transport moieties when tethered to fluorescein. As can be seen from this figure, cellular uptake generally increases when spacing increases (ε-aminocaproic acid>γ-aminobutyric acid>glycine).

Figure 2:
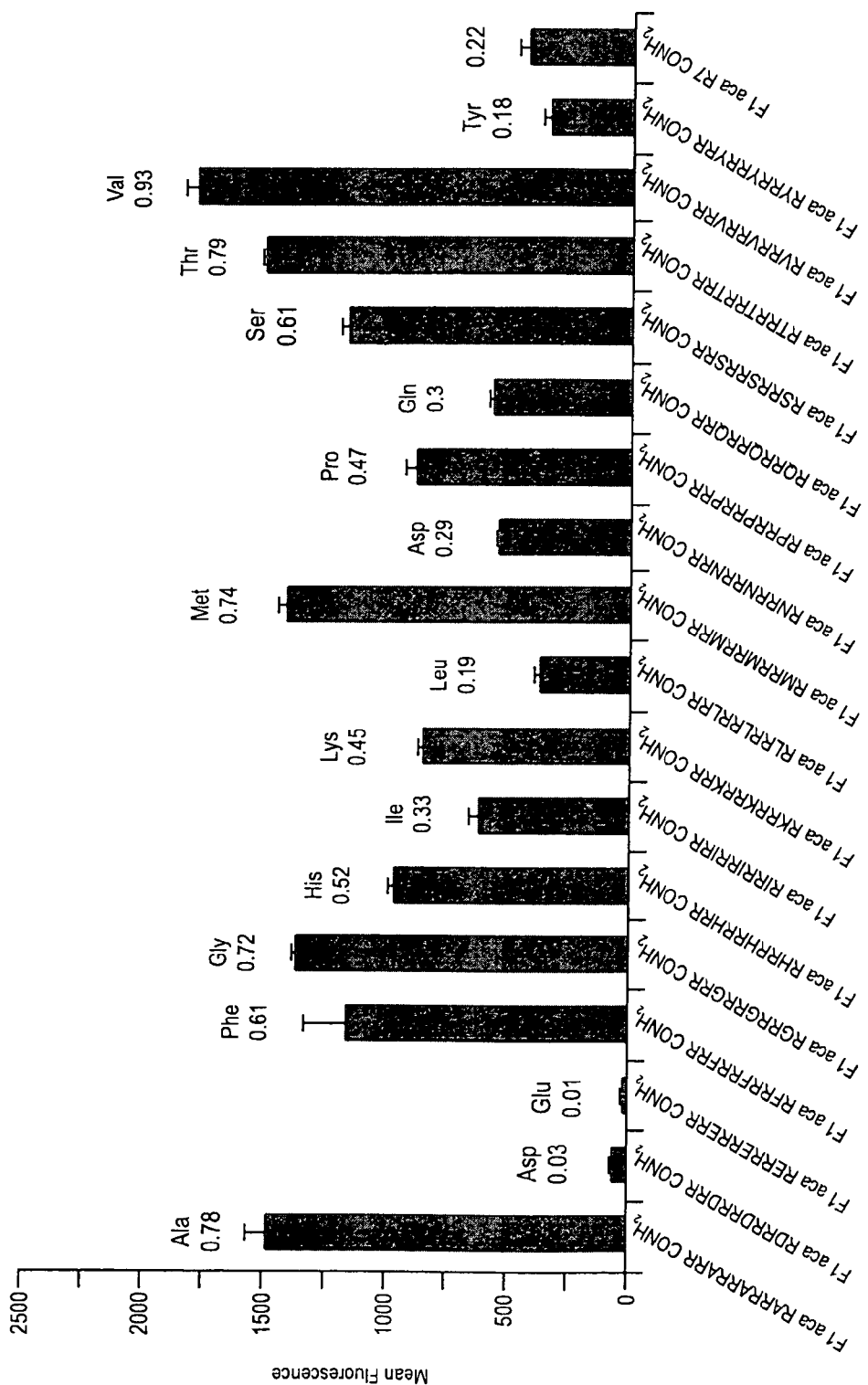
FIG. 2 is a bar graph that illustrates a general increase in cellular uptake of a fluorescence agent when a transport oligomer of spaced arginine residues is used relative to the uptake when an R7 homopolymer is the transport oligomer. The spacing groups are naturally-occurring amino acids.
Figure 3:
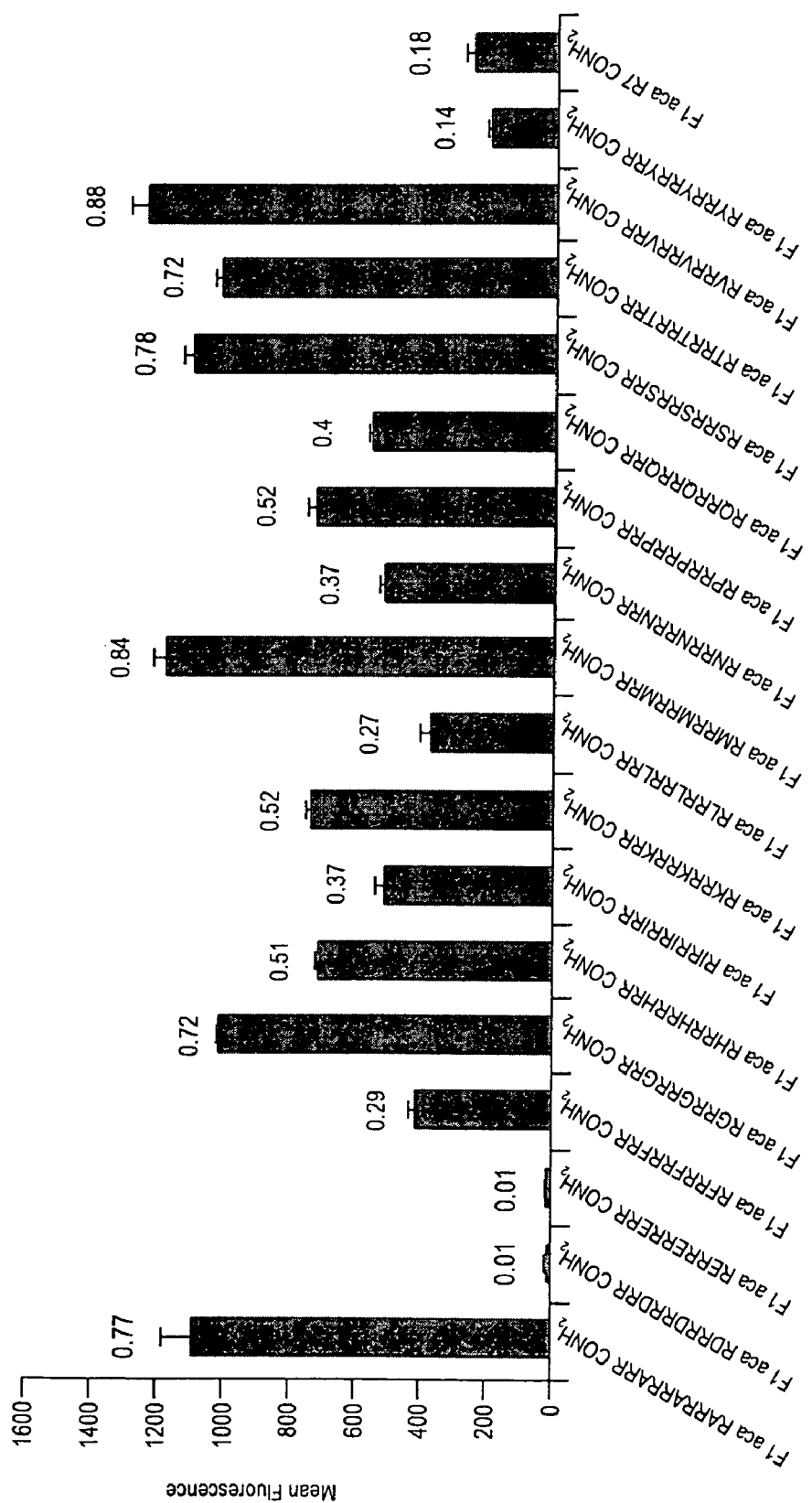
FIG. 3 is a bar graph as in FIG. 2 in which the concentrations of the various transport compositions has been reduced, illustrating that the increase in cellular uptake does not change at lower concentrations.
Figure 4:
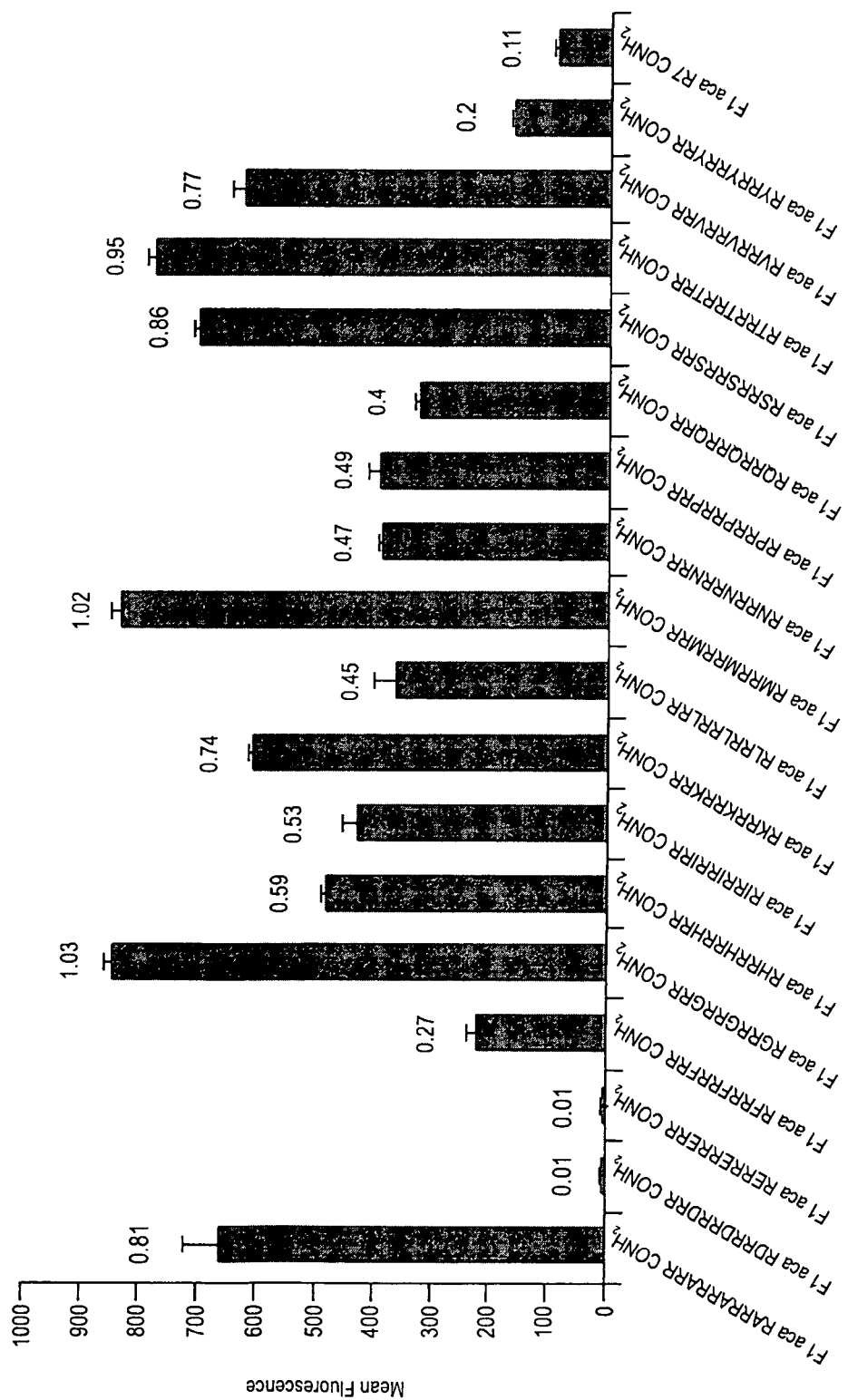
FIG. 4 is a bar graph illustrating the cellular uptake of the compositions used in FIGS. 2 and 3 at 6.25 micromolar. At this concentration, the uptake of Fl-aca-R7CONH$_2$ begins to drop off, while the compositions of the present invention maintain a significant uptake advantage.

3B—Comparison of R7 Homopolymer with Naturally-Occurring Single Amino Acid Spacing A series of arginine containing conjugates was prepared as described in Example 1 and evaluated as described in Example 2. Spacing between seven arginine residues was provided by naturally occurring (gene-encoded) amino acids (see Seq. I.D. Nos. 7 to 22). FIG. 2 shows the results of cellular uptake for these "spaced" arginine transport moieties when tethered to fluorescein. As can be seen from this figure, an increase in cellular uptake was found (relative to the homopolymer R7 having no "spacing") for those compositions containing the amino acids Alanine, Phenylalanine, Glycine, Histidine, Isoleucine, Lysine, Methionine, Asparagine, Proline, Glutamine, Serine, Threonine and Valine. Reduced, or comparable uptake was seen with those compositions containing Aspartic acid, Glutamic acid, and Tyrosine. Without intending to be bound by theory, it is thought that the carboxylic acid residues (for Asp and Glu) and the phenolic hydroxy group of Tyr may cancel or coordinate with the positively charged Arginine residue and lead to a reduction in the number of positively charged Arginines that are available to provide enhanced penetration into the cell. FIGS. 3 and 4 illustrate the same general results at different concentrations indicating that these results are essentially independent of concentration. At the lower concentration of 6.25 μM, the uptake of Fl-aca-R7-CONH$_2$ begins to drop off relative to the spaced arginine transport moieties.

3C—Comparison of (R-aca)$_x$R Transport Moieties

Figure 5:
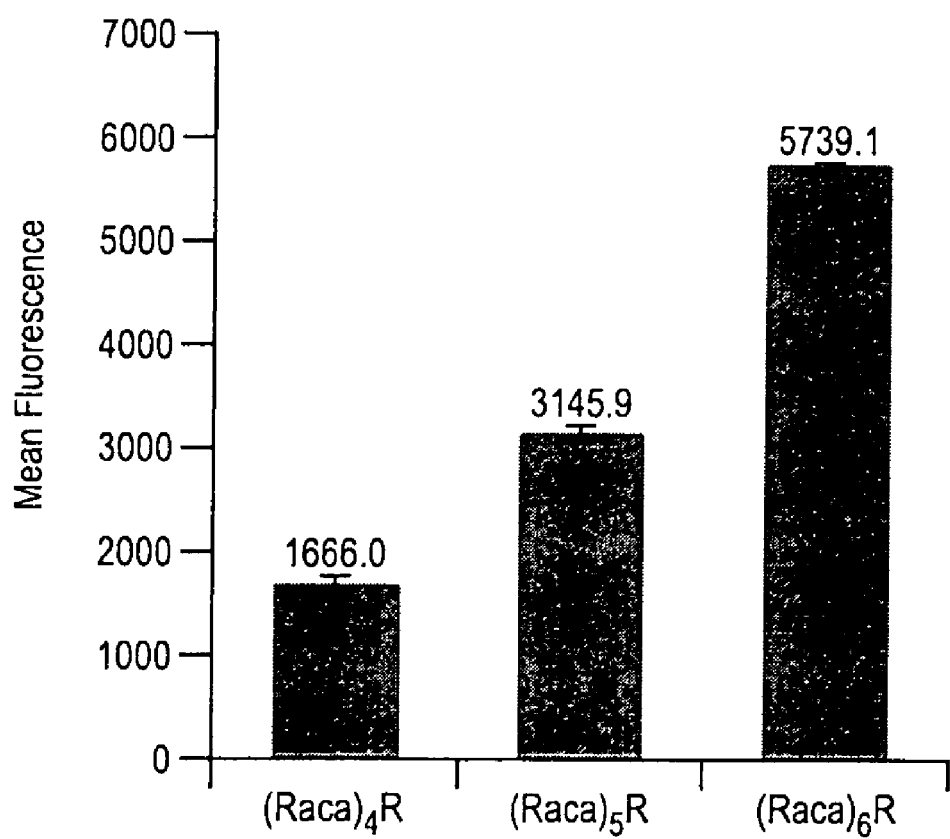
FIG. 5 is a bar graph showing the increase in cellular uptake of the series $(Raca)_xR$ at 50 µM when the subscript x is 4, 5 and 6. For brevity, the attached Fl-aca in each of the transport agents is not shown.

A series of Fl-aca-(R-aca)$_x$R compositions was prepared wherein x is 4, 5 or 6, as described in Example 1 and evaluated for cellular uptake as described in Example 2. The results are shown in FIG. 5. Here, an increase in uptake was found as overall arginine content increased (x=6>x=5>x=4).

3D—Comparison of (RX)$_6$R Versus Homopolymers of D-Arginine (r13 and r19)

Figure 6:
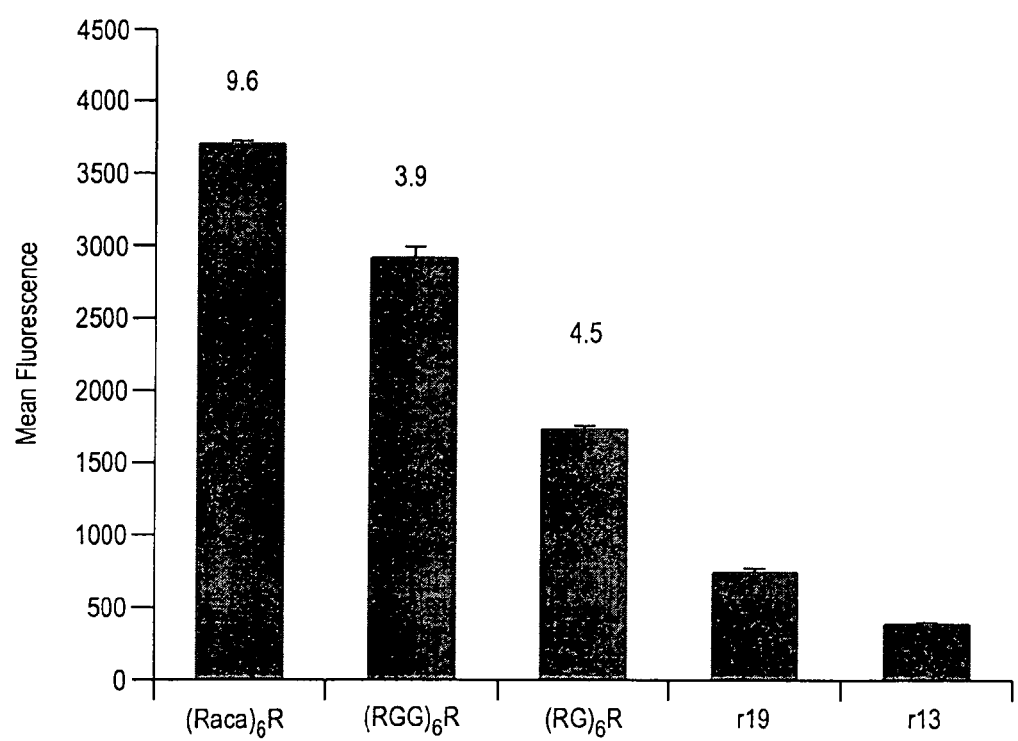
FIG. 6 is a bar graph showing the uptake (as determined by mean fluorescence) of $(RX)_6R$ transport oligomers versus homopolymers of arginine (r19 and r13). In this Figure the symbol X represents aminocaproic acid, gly-gly, or gly. For brevity, the attached Fl-aca in each of the transport agents is not shown.

A series of Fl-aca-(R—X)$_6$R compositions was prepared wherein x is aca, gly or glygly, as described in Example 1 and evaluated for cellular uptake as described in Example 2. A comparison to homopolymers of D-arginine (Fl-aca-r19-CONH$_2$ and Fl-aca-r13-CONH$_2$) was made and the results are shown in FIG. 6. The homopolymers, r13 and r19, were selected as being of equivalent length to (RG)$_6$R and (RGG)$_6$R, respectively. Surprisingly, the homopolymers were significantly less effective in entering the cells, despite the increased number of positively-charged arginine groups.

3E—Evaluation of Number and Position of Spacing Groups (aca)

Figure 8:
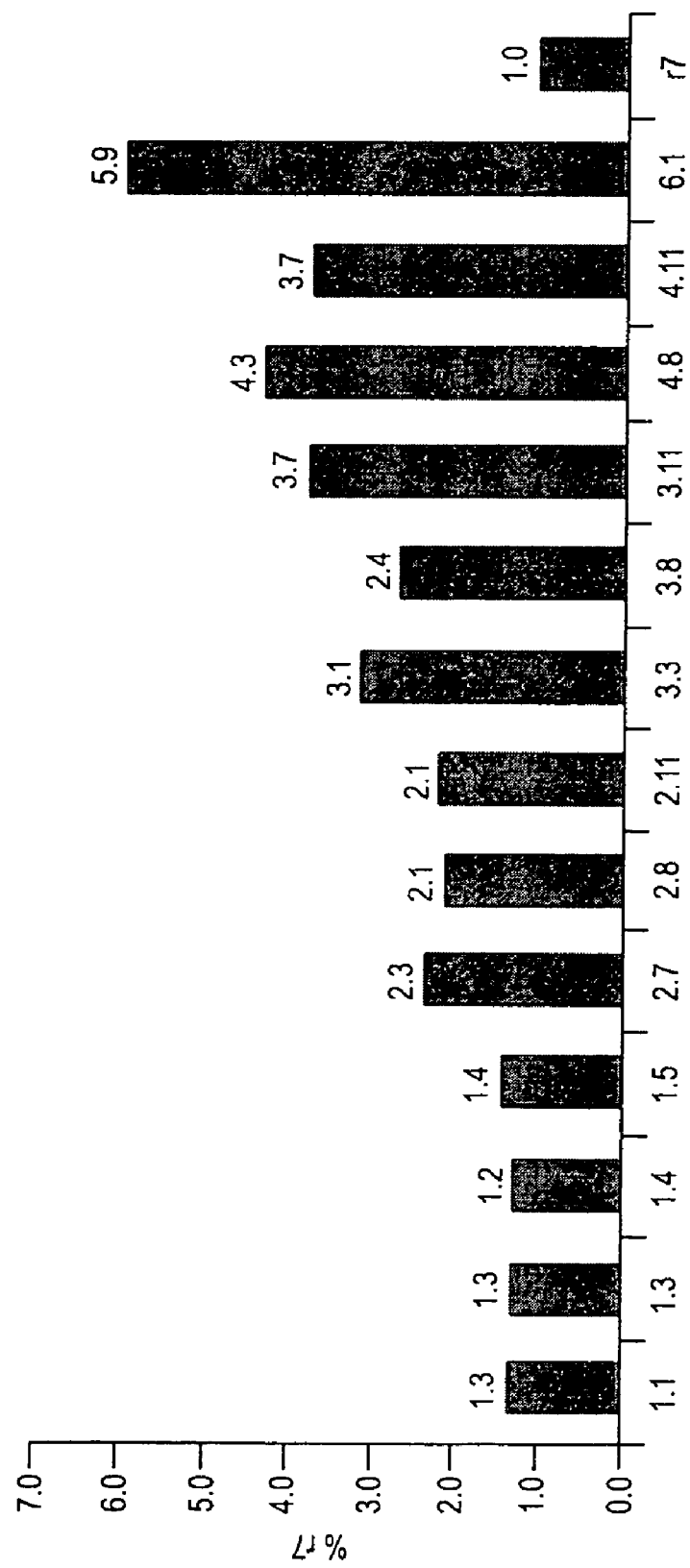
FIG. 8 is a bar graph showing the relative uptake of R aca spaced analogs relative to r7.

A entire series of Fl-aca-R7 oligomers having aca insertions within the arginine homopolymer portion was prepared as described in Example 1. The 60 peptide sequences are shown in FIG. 7. Evaluation of each compositions for cellular uptake was carried out as described in Example 2. FIG. 8 shows the results of the cellular uptake and indicates that, in general, a greater number of insertions leads to a greater uptake.

Example 4

Figure 9A:
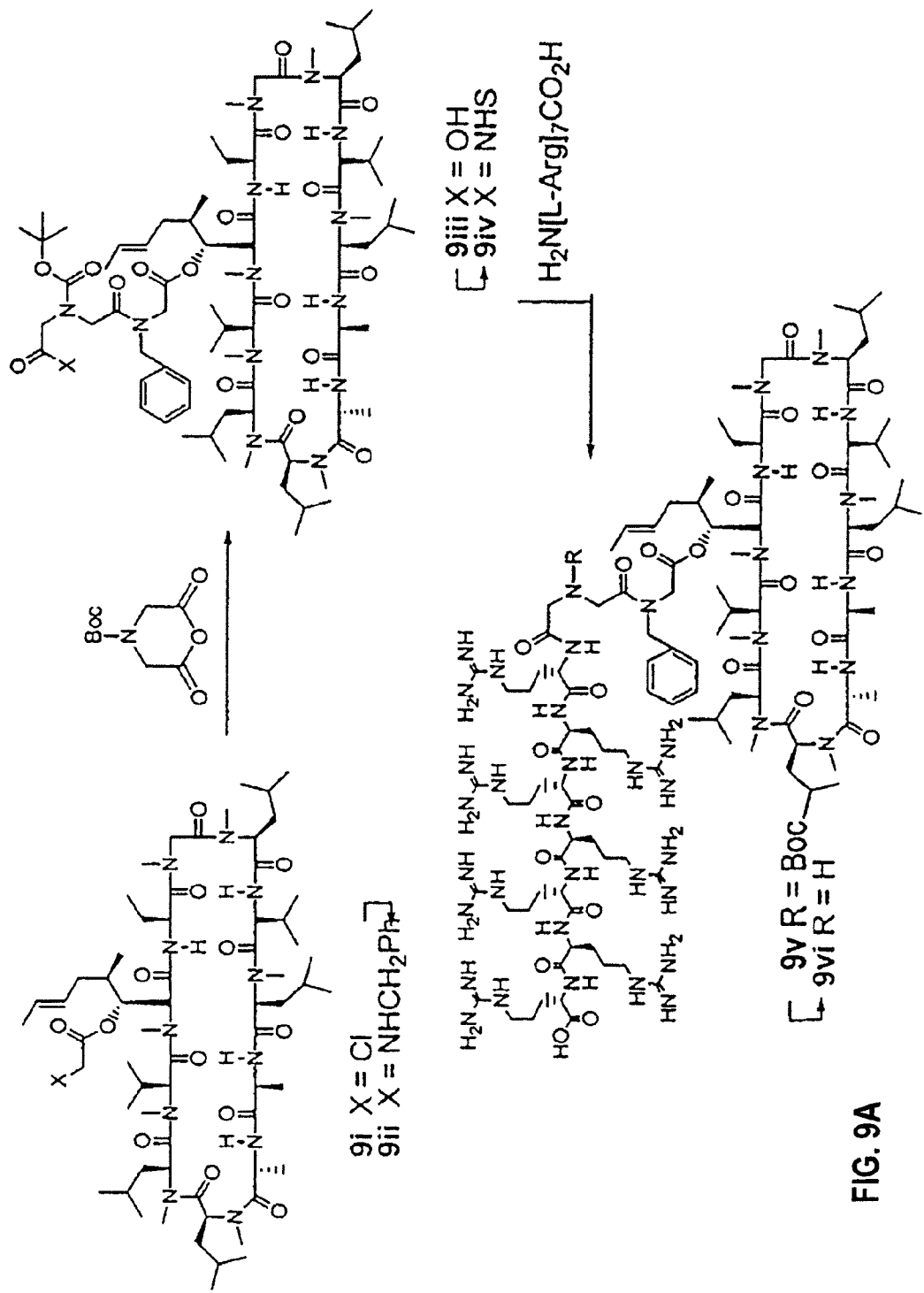
FIG. 9 illustrates the conjugation of cyclosporin to r7-acid using a self-immolating linker (see 9A). The mechanism for cleavage of the linker and release of cyclosporine as the pH decreases to 5.5 is shown in FIG. 9B.
Figure 9B:
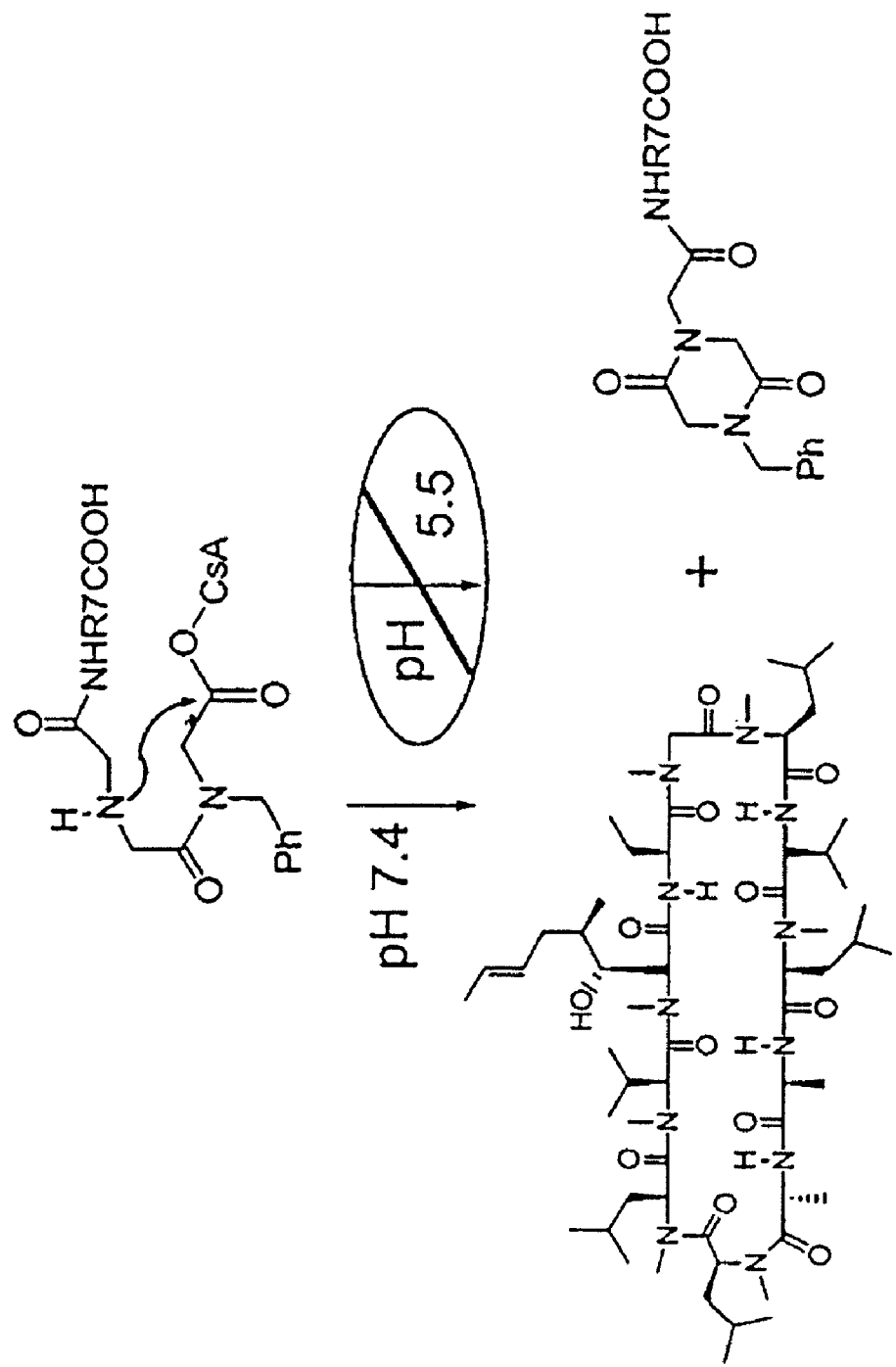

This example illustrates the conjugation of cyclosporine to a transport moiety using a pH sensitive linking group (see FIGS. 9A and 9B).

In this example, cyclosporine is converted to its α-chloroacetate ester using chloroacetic anhydride to provide 9i (see FIG. 9). The ester 9i is then treated with benzylamine to provide 9ii. Reaction of the amine with Boc-protected iminodiacetic acid anhydride provides the acid 9iii which is then converted to an activated ester (9iv) with N-hydroxy succinimide. Coupling of 9iv with L-Arginine heptamer provides the BOC-protected conjugate 9v, which can be converted to conjugate 9vi by removal of the BOC protecting group according to established methods.

Transport moieties having arginine groups separated by, for example, glycine, ε-aminocaproic acid, or γ-aminobutyric acid can be used in place of the arginine heptamer in this an in the following examples that show oligoarginine transport groups.

Example 5

This example illustrates the conjugation of acyclovir to a transport moiety.

a. Conjugation of Acyclovir to $r_7CONH_2$

This example illustrates the conjugation of acyclovir to $r_7CONH_2$ via the linking group:

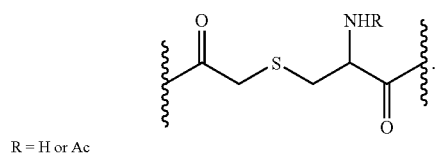

R = H or Ac i) Preparation of Acyclovir α-chloroester:

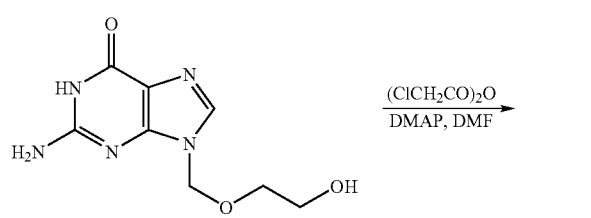

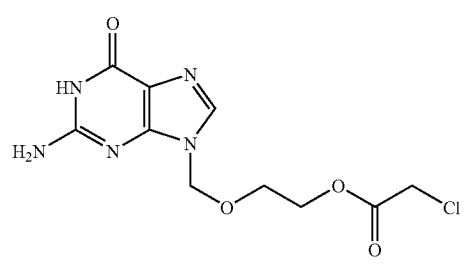

A solution of acyclovir (100 mg, 0.44 mmol), dimethylaminopyridine (5.4 mg, 0.044 mmol) and chloroacetic anhydride (226 mg, 1.32 mmol) in dimethylformamide (9 mL) was stirred at room temperature for 18 h. The dimethylformamide was removed by evaporation. The crude product was purified by reverse-phase HPLC (22 mm×250 mm C-18 column, a 5-25% $CH_3CN/H_2O$ gradient with 0.1% trifluoroacetic acid, 214 and 254 nm UV detection) and lyophilized. The product was obtained as a white powder (62 mg, 47%). $^1H$ NMR (300 MHz, DMSO-$d_6$) δ 10.67 (s, 1H), 7.88 (s, 1H), 6.53 (s, 1H), 5.27 (s, 2H), 4.35 (s, 2H), 4.21 (t, J=3 Hz, 2H), 3.70 (t, J=3 Hz, 2H); $^{13}C$ NMR (75 MHz, DMSO-$d_6$) δ 168.1, 157.6, 154.8, 152.3, 138.6, 117.1, 72.7, 67.1, 65.2, 41.8; TOF-MS (m/z): 302.0 [M+H].

ii) Conjugation of Acyclovir α-chloro Ester to $H_2N$—C-r7-$CONH_2$

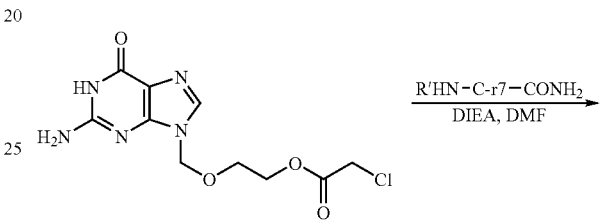

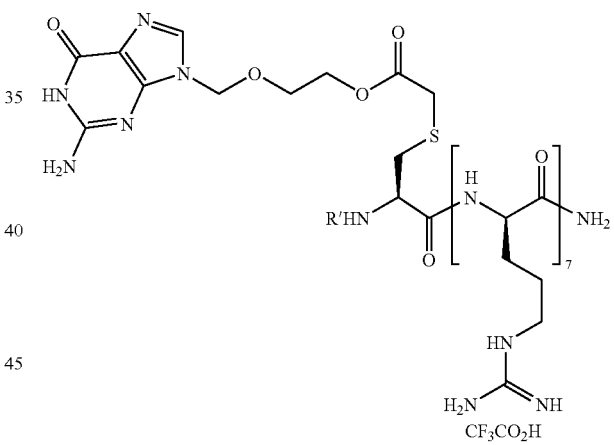

R' = H or Ac

A solution of acyclovir α-chloroester (7 mg, 0.024 mmol), $H_2N$—C-r7-$CONH_2$ (50 mg, 0.024 mmol) and diisopropylethylamine (6.4 µL, 0.036 mmol) in dimethylformamide (1 mL) was stirred for 18 h. The dimethylformamide was removed by evaporation. The crude product was purified by reverse-phase HPLC (22 mm×250 mm C-18 column, a 5-25% $CH_3CN/H_2O$ gradient with 0.1% trifluoroacetic acid, 214 and 254 nm UV detection) and lyophilized. The desired product was obtained as a white powder (24 mg, 69%). TOF-MS (m/z): 494.6 [(M+H)/3], 371.0 [(M+H)/4].

The yield could be increased by using 10 molar equivalents of diisopropylethylamine rather than 1.5 molar equivalents. Product was again obtained as a white powder (79%). TOF-MS (m/z): 508.7 [(M+H)/3], 381.5 [(M+H)/4], 305.5 [(M+H)/5].

b. Conjugation of Acyclovir to a Biotin-Containing Derivative of $r_5$-Cys—$CONH_2$

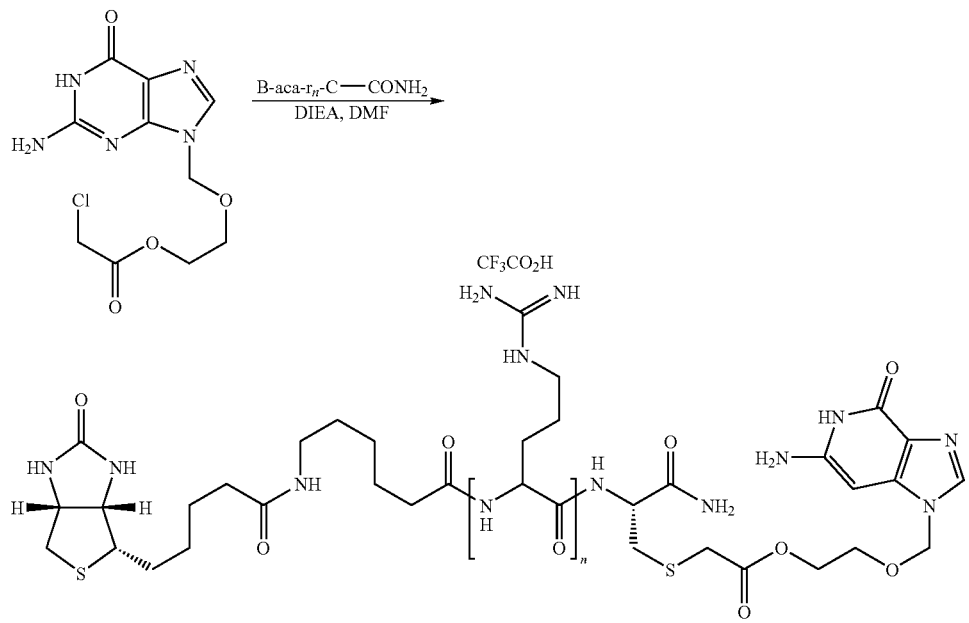

Reactions were carried out as illustrated above, using the synthetic techniques provided in the examples above.

i) Biotin-aminocaproic acid-r5-Cys(acyclovir)-$CONH_2$ was obtained as a white powder (36%). TOF-MS (m/z): 868.2 {(M+2 TFA)/2], 811.2 [(M+1 TFA)/2], 754.1 [(M+1 TFA)/3], 503.0 [(M+H)/3], 377.4 [(M+H)/4].

Similarly, ii) Biotin-aminocaproic acid-r7-C(acyclovir)-$CONH_2$— was obtained as a white powder (33%). TOF-MS (m/z):722.1 [(M+3 TFA)/3], 684.6 [(M+2 TFA)/3], 607.1 [(M+H)/3], 455.5 [(M+H)/4], 364.8 [(M+H)/5], 304.3 [(M+H)/6].

Example 6

This example illustrates the conjugation of hydrocortisone to a transport moiety.

a. Conjugation of Hydrocortisone to $r_7CONH_2$
i) Preparation of Hydrocortisone α-chloroester:

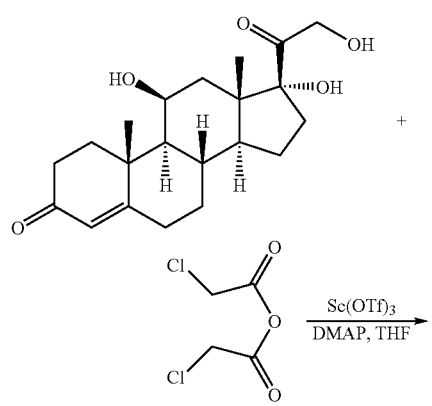

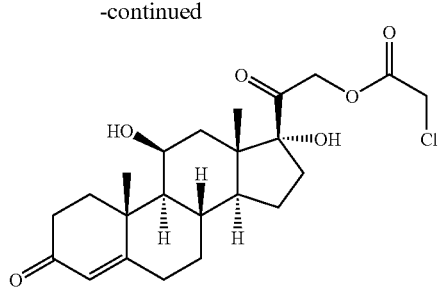

To a solution of hydrocortisone (500 mg, 1.38 mmol), scandium triflate (408 mg, 0.83 mmol) and chloroacetic anhydride (708 mg, 4.14 mmol) in dry THF was added dimethylaminopyridine (506 mg, 4.14 mmol). The solution turned bright yellow upon addition of dimethylaminopyridine. After 30 min the solvent was evaporated off and the crude material taken up into ethyl acetate (100 mL). The ethyl acetate layer was washed with 1.0 N HCl and brine. The organic phase was collected, dried ($Na_2SO_4$) and evaporated to provide the product as a white solid (533 mg, 88%). $^1H$ NMR (300 MHz, DMSO-$d_6$) δ 5.56 (s, 1H), 5.46 (s, 1H), 5.20 (d, J=18 Hz, 1H), 4.85 (d, J=18 Hz, 1H), 4.51 (s, 2H), 4.37 (br s, 1H), 4.27 (br s, 1H), 2.54-2.33 (m, 2H), 2.22-2.03 (m, 3H), 1.99-1.61 (m, 8H), 1.52-1.24 (m, 5H), 1.02-0.98 (d, J=12 Hz, 1H), 0.88-0.85 (d, J=9 Hz, 1H), 0.77 (s, 3H); $^{13}C$ NMR (75 MHz, DMSO-$d_6$) δ 205.4, 198.8, 173.0, 167.6, 122.3, 89.5, 69.7, 67.3, 56.4, 52.4, 47.8, 41.6, 39.7, 35.0, 34.3, 34.0, 33.6, 32.3, 32.0, 24.2, 21.3, 17.4; TOF-MS (m/z): 439.1 (M+H).

(Reference for acetylation-Zhao, H.; Pendri, A.; Greenwald, R. B. *J. Org. Chem.* 1998, 63, 7559-7562.)

ii) Coupling to R'NH—Cys-r$_7$-CONH$_2$

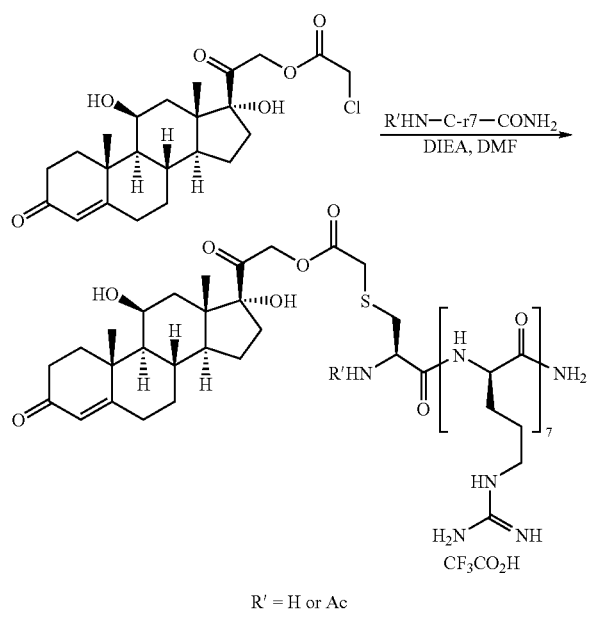

R' = H or Ac

A solution of hydrocortisone α-chloroester (31 mg, 0.071 mmol), H$_2$N—C-r7-CONH$_2$ (150 mg, 0.071 mmol) and diisopropylethylamine (15 μL, 0.085 mmol) in dimethylformamide (1 mL) was stirred for 18 h. The dimethylformamide was evaporated off. The crude product purified by reverse-phase HPLC (22 mm×250 mm C-18 column, a 5-30% CH$_3$CN/H$_2$O gradient with 0.1% trifluoroacetic acid, 214 and 254 nm UV detection) and lyophilized. The desired product was obtained as a white powder (25 mg, 14%). TOF-MS (m/z): 1037.4 [(M+4 TFA)/2], 616.1 [(M+2 TFA)/3], 578.3 [(M+1 TFA)/3], 540.5 [(M+H)/3], 405.7 [(M+H)/4], 324.5 [(M+H)/5].

The use of 10 molar equivalents of diisopropylethylamine rather than 1.2 molar equivalents provided the desired product as a yellow powder (52% yield). TOF-MS (m/z): 887.0 [(M+1 TFA)/2], 830.6 [(M+H)/2], 553.7 [(M+H)/3], 415.5 [(M+H)/4].

b. Conjugation of Hydrocortisone to a Biotin-Containing Derivative of r$_5$-Cys—CONH$_2$

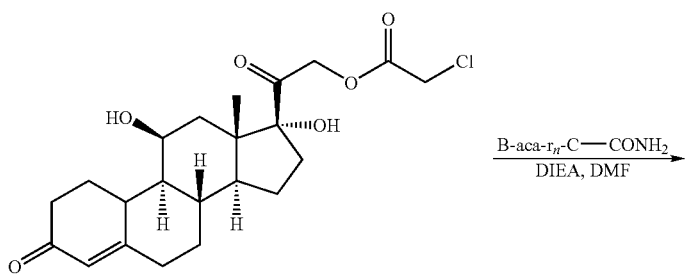

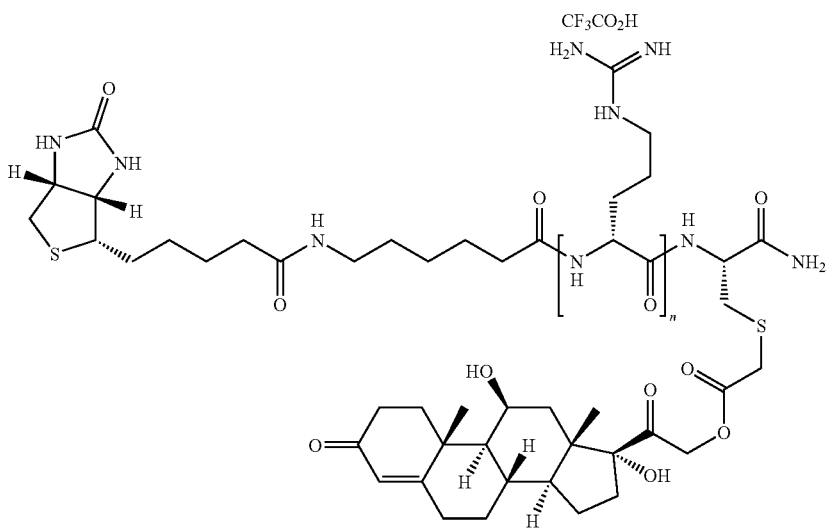

n = 5 or 7

Reactions were carried out as illustrated above, using the synthetic techniques provided in the examples above.

i) Biotin-aminocaproic acid-r5-C(hydrocortisone)-CONH$_2$— Used 10 molar equivalents of diisopropylethylamine rather than 1.2 molar equivalents. Product a white powder (65%). TOF-MS (m/z): 880.7 [(M+1 TFA)/2], 548.7 [(M+H)/3].

ii) Biotin-aminocaproic acid-r7-C(hydrocortisone)-CONH$_2$— Used 10 molar equivalents of diisopropylethylamine rather than 1.2 molar equivalents. Product a white powder (36%). TOF-MS (m/z): 692.3 [(M+1 TFA)/3], 652.8 [(M+H)/3], 520.0 [(M+1 TFA)/4], 490.0 [(M+H)/4], 392.5 [(M+H)/5].

Example 7

This example illustrates the conjugation of taxol to a transport moiety.

a. Conjugation of Taxol to r$_7$-CONH$_2$

Figure 12:
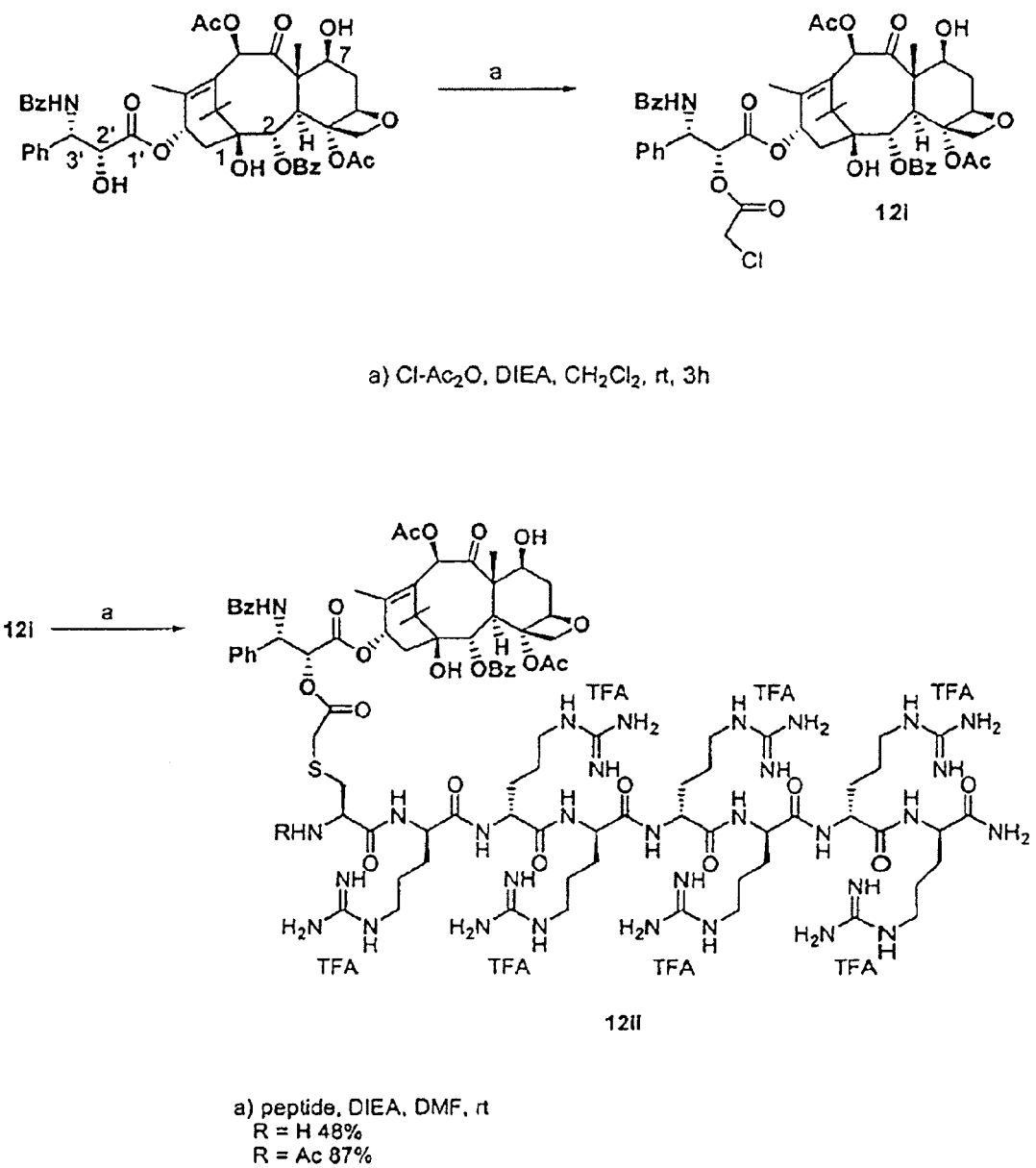
FIG. 12 illustrates the conjugation of taxol to r7-amide via an N-terminal cysteine group.

This example illustrates the application of methodology outlined above to the preparation of a taxol conjugate (see FIG. 12).

i) Preparation of a Taxol α-chloroacetate Ester

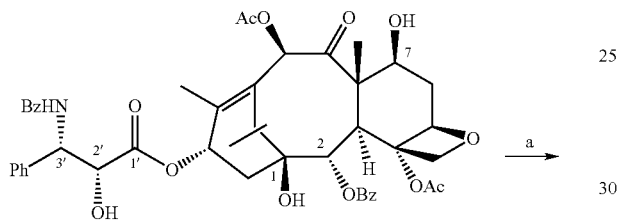

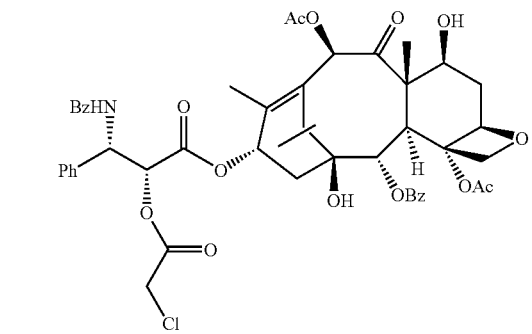

Cl—Ac$_2$O,DIEA,CH$_2$Cl$_2$,*rt*,3*h*      a)

Taxol was treated with α-chloro acetic anhydride providing the C-2' chloro acetyl derivative 12i in essentially quantitative yield.

ii) Formation of Taxol Conjugate

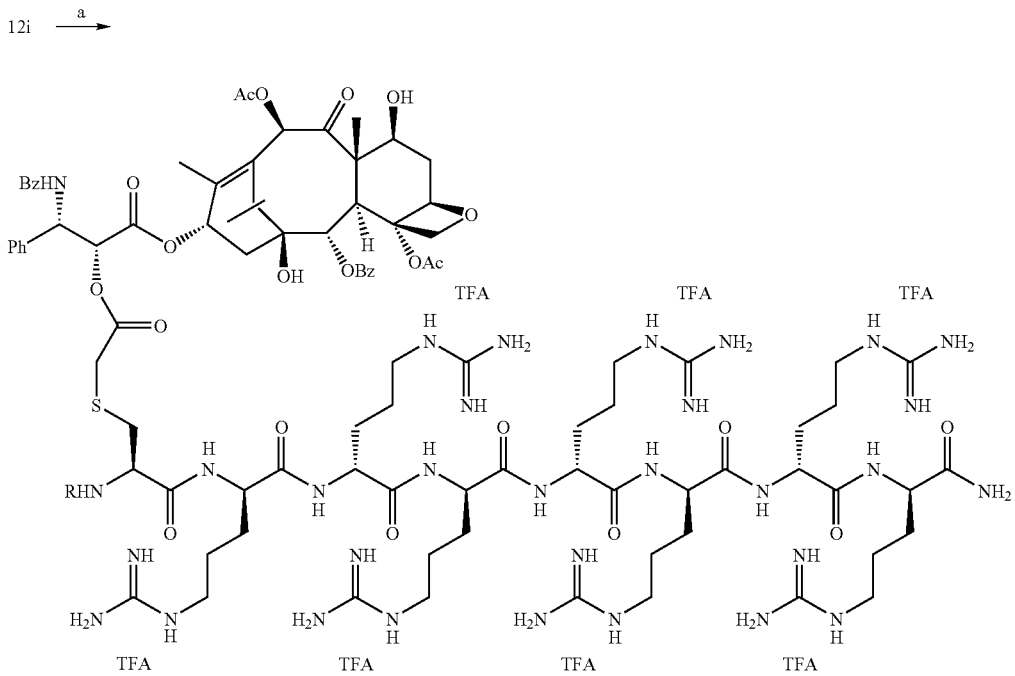

a) peptide, DIEA, DMF, rt
R = H 48%
R = Ac 87%

The halogen atom of the chloroacetate ester was displaced by the thiol of an N-terminal (L) cysteine containing heptamer of arginine. To avoid degradation of the transporter entity by proteases in-vivo, D-arginine was used as the building unit. Conjugation reactions were performed at room temperature in DMF in the presence of diisopropylethylamine. The final products were isolated by RP-HPLC and lyophilized to white powders. It is important to note that the native conjugate (R═H) is isolated as its TFA salt at the cysteine primary amine. The conjugates are generally quite hygroscopic and readily dissolve in water.

The conjugate wherein R═H was designed to release the parent drug via a nucleophilic attack of the N-terminal nitrogen onto the C2' ester carbonyl. The protonation state of this nitrogen is crucial for this mechanism, since only the free amine will be capable of this release. Additionally, both conjugates share a common α-hetero atom substituted acetate moiety making them susceptible to simple ester hydrolysis. This offers an additional release pathway.

Example 8

This example illustrates two methods of linking active agents to transport moieties. Illustration is provided for retinoic acid derivatives linked to poly-D-Arg derivatives but can be applied to linkages between other biological agents and the transport moieties of the present invention.

a. Linkage Between a Biological Agent Having an Aldehyde Functional Group

Figure 13:
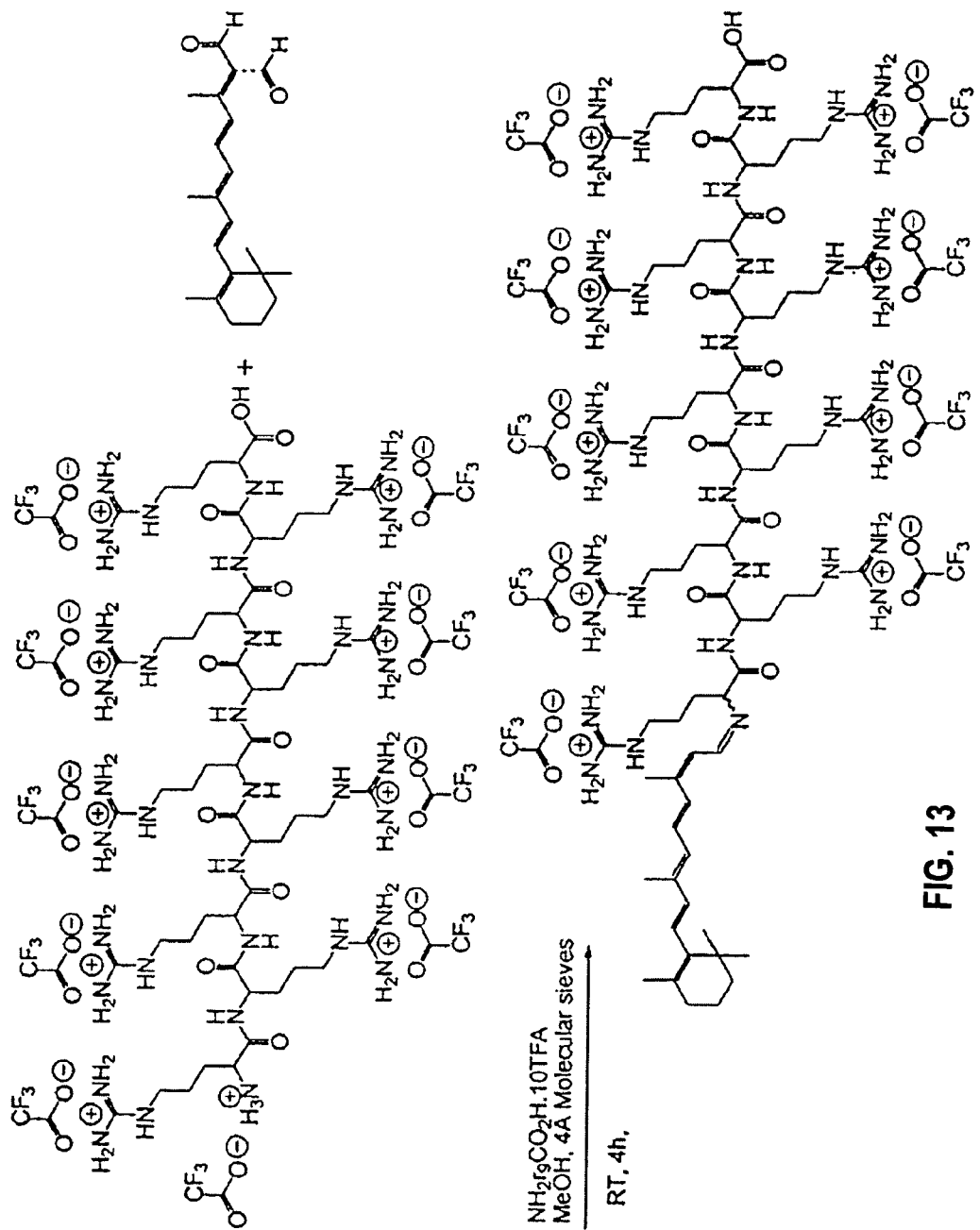
FIG. 13 illustrates the conjugate formed between a retinal and a r9 (shown without spacing amino acids).

This example illustrates the preparation of a conjugate between a nonamer of D-arginine ($H_2N$-$r_9$-$CO_2H$.10TFA) and either all trans-retinal or 13-cis-retinal. FIG. 13 provides a schematic presentation of the reactions. As seen in FIG. 13, condensation of either retinal with $H_2N$-$r_9$-$CO_2H$.10TFA in MeOH in the presence of 4 Å molecular sieves at room temperature for four hours results in the formation of a Schiff base-type linkage between the retinal aldehyde and the amino terminal group. Purification of the conjugate can be accomplished by filtering the molecular sieves and removing methanol under reduced pressure.

b. Conjugation of Retinoic Acid to $r_7$-$CONH_2$

This example illustrates the preparation of a conjugate between retinoic acid and $r_7$-$CONH_2$ using the linking group

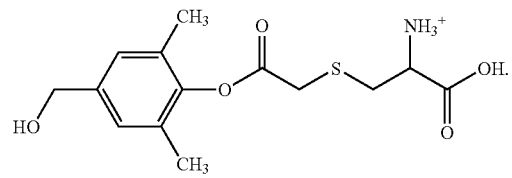

Here, preparation of the conjugate follows the scheme outlined in FIG. 14. In this scheme, retinoic acid (14ii) is first combined with the chloroacetate ester of 4-hydroxymethyl-2,6-dimethylphenol (14i) to provide the conjugate shown as 14iii. Combination of 14i with retinoic acid in methylene chloride in the presence of dicyclohexylcarbodiimide and a catalytic amount of 4-dimethylaminopyridine provided the retinoid derivative 14iii in 52-57% yield. Condensation of 14iii with $H_2NCys$-$r_7CONH_2$.8TFA in the presence of diisopropylethylamine (DMF, room temperature, 2 h) provides the desired conjugated product 14iv.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition comprising a conjugate of a biologically active compound, a transport moiety and a self-immolating linker moiety linking the biologically active compound and the transport moiety, wherein the transport moiety comprises a structure selected from the group consisting of $(ZY)_nZ$, $(ZYZ)_nZ$, $(ZYY)_nZ$, and $(ZYYY)_nZ$, wherein each Z is L-arginine or D-arginine, and each Y is independently an amino acid that does not comprise an amidino or guanidino moiety, and wherein n is an integer of from 2 to 10, wherein the conjugate has a structure selected from

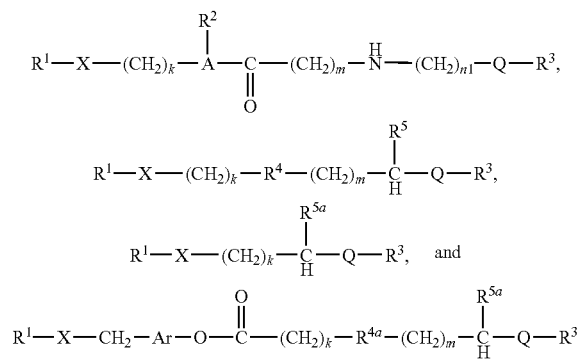

wherein
$R^1$ is the biologically active compound;
X is a linkage between a functional group on the biologically active compound and a functional group on the linker between $R^1$ and $R^3$;
Q is a linkage between a functional group on the transport moiety and a functional group on the linker between $R^1$ and $R^3$;
A is N or CH;
Ar is a substituted or unsubstituted aryl group, wherein the methylene and oxygen substituents are either ortho or para to one another;
$R^2$ is hydrogen, alkyl, aryl, arylalkyl, acyl or allyl;
$R^3$ is the transport moiety;
$R^4$ is S, O, $NR^6$ or $CR^7R^8$;
$R^{4a}$ is S, O, $NR^6$ or $CR^{7a}R^{8a}$;
$R^5$ is OH, SH, $NHR^6$, or —$CONH_2$;
$R^{5a}$ is H, OH, SH, $NHR^6$, or —$CONH_2$;
$R^6$ is hydrogen, alkyl, aryl, arylalkyl, acyl or allyl;
$R^7$ and $R^8$ are independently hydrogen, alkyl or arylalkyl; and
$R^{7a}$ and $R^{8a}$ are independently hydrogen or alkyl; and
k and m are independently either 1 or 2; and
n1 is an integer of from 1 to 10.

2. The composition according to claim 1, wherein each Y is independently selected from the group consisting of alanine, cysteine, aspartic acid, glutamic acid, phenylalanine, glycine, histidine, isoleucine, lysine, leucine, methionine, asparagine, proline, glutamine, serine, threonine, valine, tryptophan, hydroxyproline, tyrosine, γ-amino butyric acid, β-alanine, sarcosine and ε-amino caproic acid.

3. The composition according to claim 1, wherein the transport moiety comprises the structure $(ZYZ)_nZ$, and wherein n is an integer ranging from 2 to 5.

4. The composition according to claim 1, wherein the transport moiety comprises the structure $(ZY)_nZ$ and wherein n is an integer ranging from 4 to 10.

5. The composition according to claim 1, wherein the transport moiety comprises the structure $(ZYY)_nZ$, and wherein n is an integer ranging from 4 to 10.

6. The composition according to claim 1, wherein the transport moiety comprises the structure $(ZYYY)_nZ$, and wherein n is an integer ranging from 4 to 10.

7. The composition according to claim 1, wherein Y is a gene-encoded amino acid.

8. The composition according to claim 1, wherein Y is an amino acid other than a gene-encoded amino acid.

9. The composition according to claim 3, wherein each Y is independently selected from the group consisting of glycine, γ-amino butyric acid, β-alanine and ε-amino caproic acid, and n is 3 or 4.

10. A composition, comprising a conjugate of:
a biologically active compound, a transport moiety and a self-immolating linker moiety linking the biologically active compound and the transport moiety,
wherein the transport moiety comprises a structure selected from the group consisting of $(ZY)_nZ$, $(ZYZ)_nZ$, $(ZYY)_nZ$, and $(ZYYY)_nZ$,
each Z is L-arginine or D-arginine, each Y is independently glycine, γ-amino butyric acid, β-alanine or ε-amino caproic acid, and n is 6, 7 or 8, wherein the conjugate has a structure selected from

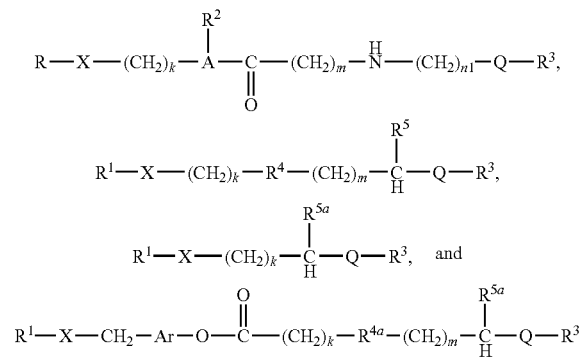

wherein
$R^1$ is the biologically active compound;
X is a linkage between a functional group on the biologically active compound and a functional group on the linker between $R^1$ and $R^3$;
Q is a linkage between a functional group on the transport moiety and a functional group on the linker between $R^1$ and $R^3$;
A is N or CH;
Ar is a substituted or unsubstituted aryl group, wherein the methylene and oxygen substituents are either ortho or para to one another;
$R^2$ is hydrogen, alkyl, aryl, arylalkyl, acyl or allyl;
$R^3$ is the transport moiety;
$R^4$ is S, O, $NR^6$ or $CR^7R^8$;
$R^{4a}$ is S, O, $NR^6$ or $CR^{7a}R^{8a}$;
$R^5$ is OH, SH, $NHR^6$, or $-CONH_2$;
$R^{5a}$ is H, OH, SH, $NHR^6$, or $-CONH_2$;
$R^6$ is hydrogen, alkyl, aryl, arylalkyl, acyl or allyl;

$R^7$ and $R^8$ are independently hydrogen, alkyl or arylalkyl; and
$R^{7a}$ and $R^{8a}$ are independently hydrogen or alkyl; and
k and m are independently either 1 or 2; and
n1 is an integer of from 1 to 10.

11. The composition according to claim 5, wherein each Y is independently selected from the group consisting of glycine, γ-amino butyric acid, β-alanine and ε-amino caproic acid, and n is 6, 7 or 8.

12. The composition according to claim 6, wherein each Y is independently selected from the group consisting of glycine, γ-amino butyric acid, β-alanine and ε-amino caproic acid, and n is 6, 7 or 8.

13. The composition according to claim 1, wherein the conjugate has the following structure:

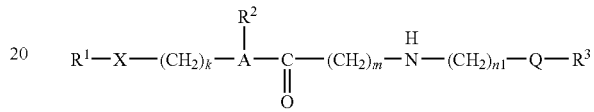

14. The composition according to claim 13, wherein each of X and Q is independently selected from the group consisting of —C(O)O—, —O—C(O)—, —C(O)NH—, —NH—C(O)—, —OC(O)NH—, —S—S—, —C(S)O—, —C(S)NH—, —NHC(O)NH—, —SO$_2$NH—, —SONH—, phosphate, phosphonate and phosphinate.

15. The composition according to claim 13, wherein each of X and Q is independently selected from the group consisting of —C(O)O—, —O—C(O)—, —C(O)NH—, —NH—C(O)—, —OC(O)NH— and —NHC(O)NH—.

16. The composition according to claim 1, wherein the conjugate has the following structure:

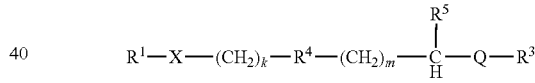

17. The composition according to claim 16 wherein each of X and Q is independently selected from the group consisting of —C(O)O—, —O—C(O)—, —C(O)NH—, —NH—C(O)—, —OC(O)NH—, —S—S—, —C(S)O—, —C(S)NH—, —NHC(O)NH—, —SO$_2$NH—, —SONH—, phosphate, phosphonate and phosphinate.

18. The composition according to claim 16, wherein each of X and Q is independently selected from the group consisting of —C(O)O—, —O—C(O)—, —C(O)NH—, —NH—C(O)—, —OC(O)NH— and —NHC(O)NH—.

19. The composition according to claim 1, wherein the conjugate has the following structure:

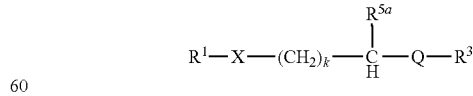

20. The composition according to claim 19, wherein each of X and Q is independently selected from the group consisting of —C(O)O—, —O—C(O)—, —C(O)NH—, —NH—C(O)—, —OC(O)NH—, —S—S—, —C(S)O—, —C(S)NH—, —NHC(O)NH—, —SO$_2$NH—, —SONH—, phosphate, phosphonate and phosphinate.

21. The composition according to claim 19, wherein each of X and Q is independently selected from the group consisting of —C(O)O—, —O—C(O)—, —C(O)NH—, —NH—C(O)—, —OC(O)NH— and —NHC(O)NH—.

22. The composition according to claim 1, wherein the conjugate has the following structure:

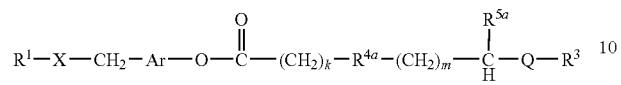

23. The composition according to claim 22, wherein each of X and Q is independently selected from the group consisting of —C(O)O—, —O—C(O)—, —C(O)NH—, —NH—C(O)—, —OC(O)NH—, —S—S—, —C(S)O—, —C(S)NH—, —NHC(O)NH—, —SO$_2$NH—, —SONH—, phosphate, phosphonate and phosphinate.

24. The composition according to claim 22, wherein each of X and Q is independently selected from the group consisting of —C(O)O—, —O—C(O)—, —C(O)NH—, —NH—C(O)—, —OC(O)NH— and —NHC(O)NH—.

25. The composition according to claim 15, wherein A is N, $R^2$ is benzyl, k, m and n1 are 1, and X is —OC(O)—.

26. A method for increasing the transport of a biologically active compound across a biological membrane comprising:
administering a composition comprising a conjugate of according to claim 1.

27. The method of claim 26, wherein the conjugate has the following structure:

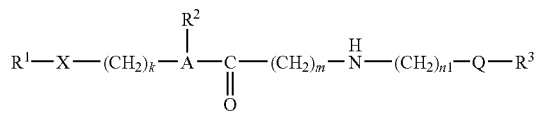

28. The method of claim 26, wherein the conjugate has the following structure:

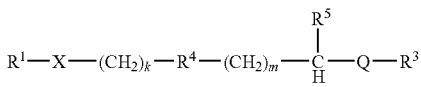

29. The method of claim 26, wherein the conjugate has the following structure:

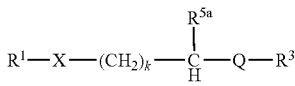

30. The method of claim 26, wherein the conjugate is of the following structure:

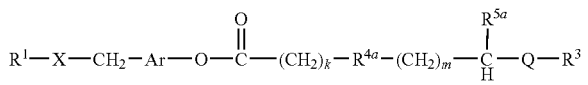

31. The composition of claim 1, wherein said linker moiety covalently links the biologically active compound and the transport moiety.

32. The composition of claim 1, wherein said linker moiety capable of self-immolation is configured so as to undergo intramolecular cleavage.

33. The composition of claim 1, wherein said linker moiety comprises a half-life in the range of between about 10 minutes and about 24 hours in water at 37° C. and at a pH of approximately 7.4.

* * * * *